US010077258B2

(12) United States Patent
Wang et al.

(10) Patent No.: US 10,077,258 B2
(45) Date of Patent: Sep. 18, 2018

(54) SUBSTITUTED PYRIMIDINE COMPOUNDS AS PHOSPHATIDYLINOSITOL 3-KINASE DELTA INHIBITOR AND USE THEREOF

(71) Applicant: NANJING SANHOME PHARMACEUTICAL CO., LTD., Nanjing, Jiangsu (CN)

(72) Inventors: Yong Wang, Nanjing (CN); Xiaorong Liu, Nanjing (CN); Dandan Huang, Nanjing (CN); Yan Zhang, Nanjing (CN); Yumei Kai, Nanjing (CN)

(73) Assignee: NANJING SANHOME PHARMACEUTICAL CO., LTD., Nanjing (CN)

( * ) Notice: Subject to any disclaimer, the term of this patent is extended or adjusted under 35 U.S.C. 154(b) by 0 days.

(21) Appl. No.: 15/551,679

(22) PCT Filed: Mar. 4, 2016

(86) PCT No.: PCT/CN2016/075618
§ 371 (c)(1),
(2) Date: Aug. 17, 2017

(87) PCT Pub. No.: WO2016/141855
PCT Pub. Date: Sep. 15, 2016

(65) Prior Publication Data
US 2018/0037576 A1 Feb. 8, 2018

(30) Foreign Application Priority Data

Mar. 6, 2015 (CN) .......................... 2015 1 0101229

(51) Int. Cl.
*C07D 405/12* (2006.01)
*C07D 401/12* (2006.01)

(52) U.S. Cl.
CPC ......... *C07D 405/12* (2013.01); *C07D 401/12* (2013.01)

(58) Field of Classification Search
CPC .......................... C07D 401/12; C07D 405/12
See application file for complete search history.

(56) References Cited

U.S. PATENT DOCUMENTS

| 3,410,851 | A | 11/1968 | Stauffer |
| 2009/0137581 | A1 | 5/2009 | Chen et al. |
| 2010/0331293 | A1 | 12/2010 | Cushing et al. |
| 2010/0331306 | A1 | 12/2010 | Bui et al. |
| 2012/0094972 | A1 | 4/2012 | Brown et al. |
| 2013/0085131 | A1 | 4/2013 | Bui et al. |
| 2013/0245005 | A1 | 9/2013 | Sorba et al. |
| 2015/0320752 | A1 | 11/2015 | Nagarathnam et al. |

FOREIGN PATENT DOCUMENTS

| CN | 103237797 | 8/2013 |
| CN | 103702989 | 4/2014 |
| EP | 0245518 | 11/1987 |
| JP | 2010-522178 A | 7/2010 |
| JP | 2010-522179 A | 7/2010 |
| JP | 2012-531436 A | 12/2012 |
| JP | 2012-531438 A | 12/2012 |
| JP | 2013-527123 A | 6/2013 |
| JP | 2013-530238 A | 7/2013 |
| WO | WO 2008/138920 | 11/2008 |
| WO | WO 2010/151735 | 12/2010 |
| WO | WO 2013/007676 | 1/2013 |

OTHER PUBLICATIONS

English translation of PCT International Search Report issued in International Application No. PCT/CN2016/075618, dated Jun. 8, 2016.
Bui et al., "Synthesis and SAR study of potent and selective PI3Kδ inhibitors," *Bioorganic & Medicinal Chemistry Letters*, 25(5):1104-1109, 2015.
Partial English translation of Official Action issued in Japanese Patent Application No. 2017-54240, dated Jul. 10, 2018.
Dyrager et al., "Design, synthesis, and biological evaluation of chromone-based p. 38 MAP kinase inhibitors," *Journal of Medicinal Chemistry*, 54(20):7427-7431, 2011.
Extended European Search Report issued in European Patent Application No. 16761082.3, dated Jul. 6, 2018.
Ghosh et al., "Benzopyrans. Part 23.[1] Nitrogen heterocycles fused with or linked to 1-benzopyran from 3-acyl-2-methyl-1-benzopyran-4-one," *Journal of the Chemical Society, Perkin Transactions 1*, 6:1489-1493, 1988.

*Primary Examiner* — Valerie Rodriguez-Garcia
(74) *Attorney, Agent, or Firm* — Parker Highlander PLLC

(57) ABSTRACT

The present invention belongs to the field of medicinal chemistry, and relates to substituted pyrimidine compounds as phosphatidylinositol 3-kinase (PI3K) δ inhibitor and a use thereof. In particular, the present invention provides a compound as shown by formula I or an isomer, pharmaceutically acceptable salt, solvate or prodrug thereof, the preparation methods of same and pharmaceutical compositions containing these compounds and a use of these compounds or compositions for treating cancer, hyperblastosis diseases or inflammatory diseases. The compounds of the present invention have a good inhibiting activity on PI3Kδ and have a high selectivity. It is hoped that these will be therapeutic agents for cancer, hyperblastosis diseases or inflammatory diseases.

17 Claims, No Drawings

SUBSTITUTED PYRIMIDINE COMPOUNDS AS PHOSPHATIDYLINOSITOL 3-KINASE DELTA INHIBITOR AND USE THEREOF

This application is a national phase application under 35 U.S.C. § 371 of International application No. PCT/CN2016/075618, titled "SUBSTITUTED PYRIMIDINE COMPOUNDS AS PHOSPHATIDYLINOSITOL 3-KINASE Δ INHIBITOR AND USE THEREOF", filed Mar. 4, 2016, which claims priority to Chinese patent application No. 201510101229.9, titled "SUBSTITUTED PYRIMIDINE COMPOUNDS AS PHOSPHATIDYLINOSITOL 3-KINASE δ INHIBITOR AND USE THEREOF", filed with the Chinese State Intellectual Property Office on Mar. 6, 2015, the entire contents of both of which are incorporated herein by reference.

FIELD

The present invention belongs to the field of pharmaceutical chemistry, in particular, relates to a class of substituted pyrimidine compounds as phosphatidylinositol 3-kinase (PI3K) δ inhibitor or isomers, pharmaceutically acceptable salts, solvates or prodrugs thereof, preparation methods of the same and pharmaceutical compositions containing these compounds and use of these compounds or compositions for treating cancers, tissue proliferative diseases or inflammatory diseases.

BACKGROUND

PI3K (phosphatidylinositol 3-kinase) is a member of the unique and conserved family of intracellular lipid kinases, which is capable of phosphorylating the 3'-OH group on phosphatidylinositols. According to different structures and substrates for phosphorylation, PI3Ks can be divided into three classes: I, II and III, wherein Class I PI3K is a hot spot in the present study. Class I PI3K plays an important role in the regulation of immune cells which have PI3K activity and are helpful for pro-tumourigenic effect of inflammatory cells (Coussens and Werb, Nature, 2002, 420, 860-867), so that it has therapeutic values for the treatment of various forms of cancerous diseases, including solid tumors (such as carcinomas and sarcomas), leukemias and lymphoid malignancies. Class I PI3K consists of p110 unit and p85 unit. At present, there are four known p110 subunits, namely p110α, p110β, p110γ and p110δ, where p110δ mainly occurs in spleen and hematopoietic cells including leukocytes such as T cells, dendritic cells, neutrophils, mast cells, B cells and macrophages. PI3Kδ is fully involved in mammalian immune system functions such as T cell function, dendritic cell function, neutrophil activity, mast cell activation, B cell activation. Thus, PI3Kδ is also involved in a variety of diseases associated with abnormal immune response, such as allergic reactions, inflammatory diseases, inflammation-mediated angiogenesis, rheumatoid arthritis, autoimmune diseases such as lupus erythematosus, asthma, emphysema and other respiratory diseases.

Drug research targeting PI3K pathway has been carried out for many years and has certain clinical success. Particularly, the recent discovery found that selective PI3Kδ inhibitors have a significant effect in the treatment of cancer and other diseases. However, there residue a need to develop superior PI3K inhibitors, particularly selective PI3Kδ inhibitors, to specifically regulate and/or mediate the transduction of PI3K and related protein kinases in order to be used in the treatment of diseases associated with PI3K kinase-mediated events.

SUMMARY

One object of the present invention is to provide a compound of formula I, which has PI3K inhibitory activity or an isomer, pharmaceutically acceptable salt, solvate or prodrug thereof,

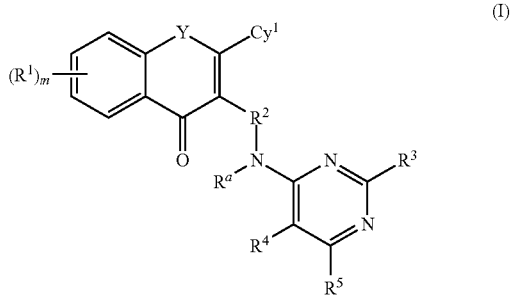

wherein,

Y is selected from the group consisting of O and N($R^b$), wherein $R^b$ is selected from the group consisting of hydrogen, alkyl, haloalkyl and cycloalkyl;

$R^1$ is selected from the group consisting of hydrogen, hydroxy, halogen, alkyl, haloalkyl, hydroxyalkyl, alkoxy, nitro, carboxyl, cyano, amino, monoalkylamino and dialkylamino; m is selected from the group consisting of 1, 2, 3 and 4;

$R^2$ is selected from the group consisting of alkylene, alkenylene, alkynylene and cycloalkylene, which are optionally substituted with one or more of alkyl, haloalkyl, hydroxy, hydroxyalkyl, halogen, oxo, alkoxy, carboxyl, cyano, amino, monoalkylamino or dialkylamino;

$Cy^1$ is selected from the group consisting of aryl and heteroaryl, which are optionally substituted with one or more of selected from the group consisting of halogen, hydroxy, oxo, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino or alkylacylaminoalkyl;

$R^a$ is selected from the group consisting of H and alkyl; and $R^3$, $R^4$ and $R^5$ are each independently selected from the group consisting of hydrogen, halogen, hydroxy, oxo, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino or alkylacylaminoalkyl.

Another object of the present invention is to provide a method for preparing the compound of formula I or an isomer, pharmaceutically acceptable salt, solvate or prodrug thereof.

A further object of the present invention is to provide a composition comprising the compound of formula I or an isomer, pharmaceutically acceptable salt, solvate or prodrug thereof, and a composition comprising the compound of formula I or an isomer, pharmaceutically acceptable salt, solvate or prodrug thereof and one or more PI3K inhibitors.

Another object of the present invention is to provide a method of the compound of formula I or an isomer, pharmaceutically acceptable salt, solvate or prodrug thereof in the treatment and/or prevention of cancer, tissue proliferative disease or inflammatory disease, and a use of the compound of formula I or an isomer, pharmaceutically acceptable salt, solvate or prodrug thereof in the manufacture of a medicament for the treatment and/or prevention of cancer, tissue proliferative disease or inflammatory disease.

According to the above objects, the present invention provides the following technical solutions:

The first aspect of the present invention provides a compound of formula I or an isomer, pharmaceutically acceptable salt, solvate or prodrug thereof,

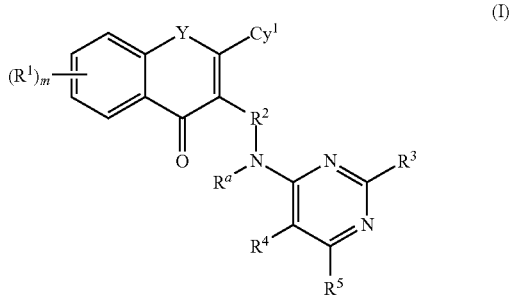

wherein,

Y is selected from the group consisting of O and $N(R^b)$, wherein $R^b$ is selected from the group consisting of hydrogen, alkyl, haloalkyl and cycloalkyl;

$R^1$ is selected from the group consisting of hydrogen, hydroxy, halogen, alkyl, haloalkyl, hydroxyalkyl, alkoxy, nitro, carboxyl, cyano, amino, monoalkylamino and dialkylamino; m is selected from the group consisting of 1, 2, 3 and 4;

$R^2$ is selected from the group consisting of alkylene, alkenylene, alkynylene and cycloalkylene, which are optionally substituted with one or more selected from the group consisting of alkyl, haloalkyl, hydroxy, hydroxyalkyl, halogen, oxo, alkoxy, carboxyl, cyano, amino, monoalkylamino or dialkylamino;

$Cy^1$ is selected from the group consisting of aryl and heteroaryl, which are optionally substituted with one or more selected from the group consisting of halogen, hydroxy, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino or alkylacylaminoalkyl;

$R^a$ is selected from the group consisting of H and alkyl; and $R^3$, $R^4$ and $R^5$ are each independently selected from the group consisting of hydrogen, halogen, hydroxy, oxo, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino or alkylacylaminoalkyl.

In some preferred embodiments, the compound of the present invention is the compound represented by formula I or an isomer, pharmaceutically acceptable salt, solvate or prodrug thereof, wherein Y is selected from the group consisting of O and $N(R^b)$, wherein $R^b$ is selected from the group consisting of hydrogen, $(C_{1-6})$alkyl, halo$(C_{1-6})$alkyl and $(C_{3-6})$cycloalkyl;

more preferably, Y is selected from the group consisting of O and $N(R^b)$, wherein $R^b$ is selected from the group consisting of hydrogen, $(C_{1-3})$alkyl, halo$(C_{1-3})$alkyl and $(C_{3-6})$cycloalkyl;

even more preferably, Y is selected from the group consisting of O and $N(R^b)$, wherein $R^b$ is selected from the group consisting of hydrogen, methyl, ethyl, propyl, isopropyl, cyclopropyl, cyclobutyl, cyclopentyl and cyclohexyl.

In some specific embodiments, the compound of the present invention is the compound of formula I or an isomer, pharmaceutically acceptable salt, solvate or prodrug thereof, wherein Y is O.

In other specific embodiments, the compound of the present invention is the compound of formula I or an isomer, pharmaceutically acceptable salt, solvate or prodrug thereof, wherein Y is $N(R^b)$, and $R^b$ is selected from the group consisting of hydrogen, methyl, ethyl and cyclopropyl.

In some preferred embodiments, the compound of the present invention is the compound of formula I or an isomer, pharmaceutically acceptable salt, solvate or prodrug thereof, wherein $R^1$ is selected from the group consisting of hydrogen, hydroxy, halogen, $(C_{1-6})$alkyl, halo$(C_{1-6})$alkyl, hydroxy $(C_{1-6})$alkyl, $(C_{1-6})$alkoxy, nitro, carboxyl, cyano, amino, mono-$(C_{1-6})$alkylamino and di-$(C_{1-6})$alkylamino;

more preferably, $R^1$ is selected from the group consisting of hydrogen, hydroxy, halogen, $(C_{1-3})$alkyl, halo$(C_{1-3})$alkyl, hydroxy$(C_{1-3})$alkyl, $(C_{1-3})$alkoxy, nitro, carboxyl, cyano, amino, mono-$(C_{1-3})$alkylamino and di-$(C_{1-3})$alkylamino;

even more preferably, $R^1$ is selected from the group consisting of hydrogen, hydroxy, halogen, methyl, ethyl, propyl, isopropyl, trifluoromethyl, hydroxymethyl, methoxy, nitro, carboxyl, cyano, amino, methylamino and dimethylamino.

In some preferred embodiments, the compound of the present invention is the compound of formula I or an isomer, pharmaceutically acceptable salt, solvate or prodrug thereof, wherein $R^2$ is selected from the group consisting of $(C_{1-10})$alkylene, $(C_{3-10})$cycloalkylene, $(C_{2-10})$alkenylene and $(C_{2-10})$alkynylene, which are optionally substituted with one or more selected from the group consisting of $(C_{1-6})$alkyl, halo$(C_{1-6})$alkyl, hydroxy, hydroxy$(C_{1-6})$alkyl, halogen, oxo, $(C_{1-6})$alkoxy, carboxyl, cyano, amino, mono-$(C_{1-6})$alkylamino or di-$(C_{1-6})$alkylamino;

more preferably, $R^2$ is selected from the group consisting of $(C_{1-6})$alkylene, $(C_{3-6})$cycloalkylene, $(C_{2-6})$alkenylene and $(C_{2-6})$alkynylene, which are optionally substituted with one or more selected from the group consisting of $(C_{1-3})$alkyl, halo$(C_{1-3})$alkyl, hydroxy, hydroxy$(C_{1-3})$alkyl, halogen, oxo, $(C_{1-3})$alkoxy, carboxyl, cyano, amino, mono-$(C_{1-3})$ alkylamino or di-$(C_{1-3})$alkylamino;

even more preferably, $R^2$ is $C_{1-3}$ alkylene, which is optionally substituted with one or more selected from the group consisting of $(C_{1-3})$alkyl, halo$(C_{1-3})$alkyl, hydroxy, hydroxy$(C_{1-3})$alkyl, halogen, oxo, $(C_{1-3})$alkoxy, carboxyl, cyano, amino, mono-$(C_{1-3})$alkylamino or di-$(C_{1-3})$alkylamino.

In some specific embodiments, the compound of the present invention is the compound of formula I or an isomer, pharmaceutically acceptable salt, solvate or prodrug thereof, wherein
$R^2$ is selected from the group consisting of methylene, ethylene, propylene, cyclopropylene, cyclobutylene, cyclopentylene, cyclohexylene, vinylene, propenylene, butenylene, pentenylene, hexenylene, ethynylene, propynylene, butynylene, pentynylene and hexynylene, which are optionally substituted with one or more selected from the group consisting of methyl, ethyl, propyl, isopropyl and oxo group.

In some preferred embodiments, the compound of the present invention is the compound represented by formula I or an isomer, pharmaceutically acceptable salt, solvate or prodrug thereof, wherein
$Cy^1$ is selected from the group consisting of aryl and heteroaryl, which are optionally substituted with one or more selected from the group consisting of halogen, hydroxy, amino, carboxyl, cyano, nitro, $(C_{1-6})$alkyl, $(C_{3-8})$cycloalkyl, $(C_{3-8})$heterocycloalkyl, $(C_{1-6})$alkoxy, halo$(C_{1-6})$alkyl, hydroxy$(C_{1-6})$alkyl, amino$(C_{1-6})$alkyl, carboxy$(C_{1-6})$alkyl, cyano$(C_{1-6})$alkyl, nitro$(C_{1-6})$alkyl, cycloalkyl$(C_{1-6})$alkyl, $(C_{3-8})$heterocycloalkyl$(C_{1-6})$alkyl, $(C_{1-6})$alkoxy$(C_{1-6})$alkyl, mono-$(C_{1-6})$alkylamino, mono-$(C_{1-6})$alkylamino$(C_{1-6})$alkyl, di-$(C_{1-6})$alkylamino, di-$(C_{1-6})$alkylamino$(C_{1-6})$alkyl, $(C_{1-6})$alkylacyl, $(C_{1-6})$alkylacyl$(C_{1-6})$alkyl, $(C_{1-6})$alkoxyacyl, $(C_{1-6})$alkoxyacyl$(C_{1-6})$alkyl, $(C_{1-6})$alkylacyloxy, $(C_{1-6})$alkylacyloxy$(C_{1-6})$alkyl, aminoacyl, aminoacyl$(C_{1-6})$alkyl, mono-$(C_{1-6})$alkylaminoacyl, mono-$(C_{1-6})$alkylaminoacyl$(C_{1-6})$alkyl, di-$(C_{1-6})$alkylaminoacyl, di-$(C_{1-6})$alkylaminoacyl$(C_{1-6})$alkyl, $(C_{1-6})$alkylacylamino or $(C_{1-6})$alkylacylamino$(C_{1-6})$alkyl;

more preferably, $Cy^1$ is selected from the group consisting of phenyl, pyridyl, pyrimidinyl, pyrrolyl, thienyl, furyl, indolyl, isoindolyl and quinolinyl, which are optionally substituted with one or more selected from the group consisting of halogen, hydroxy, amino, carboxyl, cyano, nitro, $(C_{1-6})$alkyl, $(C_{3-8})$cycloalkyl, $(C_{3-8})$heterocycloalkyl, $(C_{1-6})$alkoxy, halo$(C_{1-6})$alkyl, hydroxy$(C_{1-6})$alkyl, amino$(C_{1-6})$alkyl, carboxy$(C_{1-6})$alkyl, cyano$(C_{1-6})$alkyl, nitro$(C_{1-6})$alkyl, $(C_{3-8})$cycloalkyl$(C_{1-6})$alkyl, $(C_{3-8})$heterocycloalkyl$(C_{1-6})$alkyl, $(C_{1-6})$alkoxy$(C_{1-6})$alkyl, mono-$(C_{1-6})$alkylamino, mono-$(C_{1-6})$alkylamino$(C_{1-6})$alkyl, di-$(C_{1-6})$alkylamino, di-$(C_{1-6})$alkylamino$(C_{1-6})$alkyl, $(C_{1-6})$alkylacyl, $(C_{1-6})$alkylacyl$(C_{1-6})$alkyl, $(C_{1-6})$alkoxyacyl, $(C_{1-6})$alkoxyacyl$(C_{1-6})$alkyl, $(C_{1-6})$alkylacyloxy, $(C_{1-6})$alkylacyloxy$(C_{1-6})$alkyl, aminoacyl, aminoacyl$(C_{1-6})$alkyl, mono-$(C_{1-6})$alkylaminoacyl, mono-$(C_{1-6})$alkylaminoacyl$(C_{1-6})$alkyl, di-$(C_{1-6})$alkylaminoacyl, di-$(C_{1-6})$alkylaminoacyl$(C_{1-6})$alkyl, $(C_{1-6})$alkylacylamino or $(C_{1-6})$alkylacylamino$(C_{1-6})$alkyl;

even more preferably, $Cy^1$ is selected from the group consisting of phenyl, pyridyl and pyrimidinyl, which are optionally substituted with one or more selected from the group consisting of halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl$(C_{1-3})$alkyl, $(C_{1-3})$alkylacylamino or $(C_{1-3})$alkylacylamino$(C_{1-3})$alkyl.

In some preferred embodiments, the compound of the present invention is the compound of formula I or an isomer, pharmaceutically acceptable salt, solvate or prodrug thereof, wherein $R^a$ is selected from the group consisting of hydrogen and $C_{1-6}$ alkyl, and more preferably, $R^a$ is selected from the group consisting of hydrogen and $C_{1-3}$ alkyl, and even more preferably, $R^a$ is selected from the group consisting of H, methyl, ethyl and propyl.

In some preferred embodiments, the compound of the present invention is the compound of formula I or an isomer, pharmaceutically acceptable salt, solvate or prodrug thereof, wherein
$R^3$, $R^4$ and $R^5$ are each independently selected from the group consisting of hydrogen, halogen, hydroxy, oxo, amino, carboxyl, cyano, nitro, $(C_{1-6})$alkyl, $(C_{3-6})$cycloalkyl, $(C_{3-6})$heterocycloalkyl, $(C_{1-6})$alkoxy, halo$(C_{1-6})$alkyl, hydroxy$(C_{1-6})$alkyl, amino$(C_{1-6})$alkyl, carboxy$(C_{1-6})$alkyl, cyano$(C_{1-6})$alkyl, nitro$(C_{1-6})$alkyl, $(C_{3-6})$cycloalkyl$(C_{1-6})$alkyl, $(C_{3-6})$heterocycloalkyl$(C_{1-6})$alkyl, $(C_{1-6})$alkoxy$(C_{1-6})$alkyl, mono-$(C_{1-6})$alkylamino, mono-$(C_{1-6})$alkylamino$(C_{1-6})$alkyl, di-$(C_{1-6})$alkylamino, di-$(C_{1-6})$alkylamino$(C_{1-6})$alkyl, $(C_{1-6})$alkylacyl, $(C_{1-6})$alkylacyl$(C_{1-6})$alkyl, $(C_{1-6})$alkoxyacyl, $(C_{1-6})$alkoxyacyl$(C_{1-6})$alkyl, $(C_{1-6})$alkylacyloxy, $(C_{1-6})$alkylacyloxy$(C_{1-6})$alkyl, aminoacyl, aminoacyl$(C_{1-6})$alkyl, mono-$(C_{1-6})$alkylaminoacyl, mono-$(C_{1-6})$alkylaminoacyl$(C_{1-6})$alkyl, di-$(C_{1-6})$alkylaminoacyl, di-$(C_{1-6})$alkylaminoacyl$(C_{1-6})$alkyl, $(C_{1-6})$alkylacylamino and $(C_{1-6})$alkylacylamino$(C_{1-6})$alkyl;

more preferably, $R^3$, $R^4$ and $R^5$ are each independently selected from the group consisting of hydrogen, halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino and $(C_{1-3})$alkylacylamino$(C_{1-3})$alkyl.

In some specific embodiments, the compound of the present invention is the compound of formula I or an isomer, pharmaceutically acceptable salt, solvate or prodrug thereof, wherein
Y is selected from the group consisting of O and $N(R^b)$, wherein $R^b$ is selected from the group consisting of hydrogen, methyl, ethyl, propyl, isopropyl, cyclopropyl, cyclobutyl, cyclopentyl and cyclohexyl;

R[1] is selected from the group consisting of hydrogen, hydroxy, halogen, $(C_{1-3})$alkyl, halo$(C_{1-3})$alkyl, hydroxy$(C_{1-3})$alkyl, $(C_{1-3})$alkoxy, nitro, carboxyl, cyano, amino, mono-$(C_{1-3})$alkylamino and di-$(C_{1-3})$alkylamino; m is selected from the group consisting of 1, 2, 3 and 4;

R[2] is selected from the group consisting of methylene, ethylene, propylene, cyclopropylene, cyclobutylene, cyclopentylene, cyclohexylene, vinylene, propenylene, butenylene, pentenylene, hexenylene, ethynylene, propynylene, butynylene, pentynylene and hexynylene, which are optionally substituted with one or more selected from the group consisting of methyl, ethyl, propyl, isopropyl and oxo;

Cy[1] is selected from the group consisting of phenyl, pyridyl and pyrimidinyl, which are optionally substituted with one or more selected from the group consisting of halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino or $(C_{1-3})$alkylacylamino$(C_{1-3})$alkyl;

R[a] is selected from the group consisting of H, methyl, ethyl and propyl; and

R[3], R[4] and R[5] are each independently selected from the group consisting of hydrogen, halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino and $(C_{1-3})$alkylacylamino$(C_{1-3})$alkyl.

In other specific embodiments, the compound of the present invention is the compound of formula I or an isomer, pharmaceutically acceptable salt, solvate or prodrug thereof, wherein Y is selected from the group consisting of O and N(R[b]), wherein R[b] is selected from the group consisting of hydrogen, methyl, ethyl, propyl, isopropyl and cyclopropyl;

R[1] is selected from the group consisting of hydrogen, hydroxyl, fluoro, chloro, methyl, ethyl, propyl, isopropyl, trifluoromethyl, hydroxymethyl, methoxy, ethoxy, nitro, carboxyl, cyano, amino, methylamino and dimethylamino; m is selected from the group consisting of 1, 2, 3 and 4;

R[2] is selected from the group consisting of methylene and ethylene, which are optionally substituted with one or more selected from the group consisting of methyl, ethyl, propyl, isopropyl and oxo group;

Cy[1] is phenyl, which is optionally substituted with one or more selected from the group consisting of halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino or $(C_{1-3})$alkylacylamino$(C_{1-3})$alkyl;

R[a] is H; and

R[3], R[4] and R[5] are each independently selected from the group consisting of hydrogen, halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino and $(C_{1-3})$alkylacylamino$(C_{1-3})$alkyl.

The present invention provides the following specific compounds:

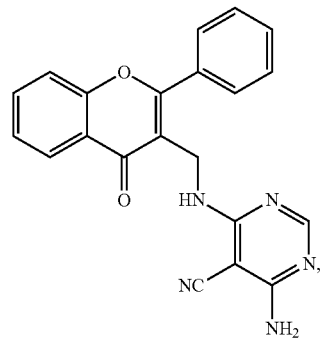

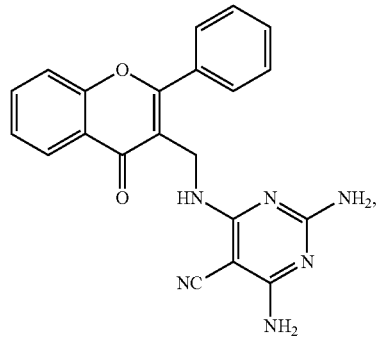

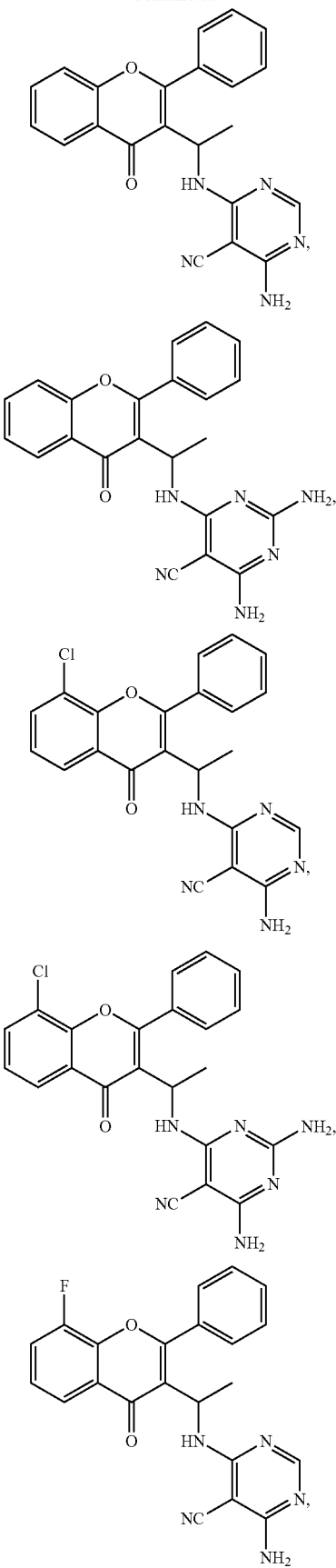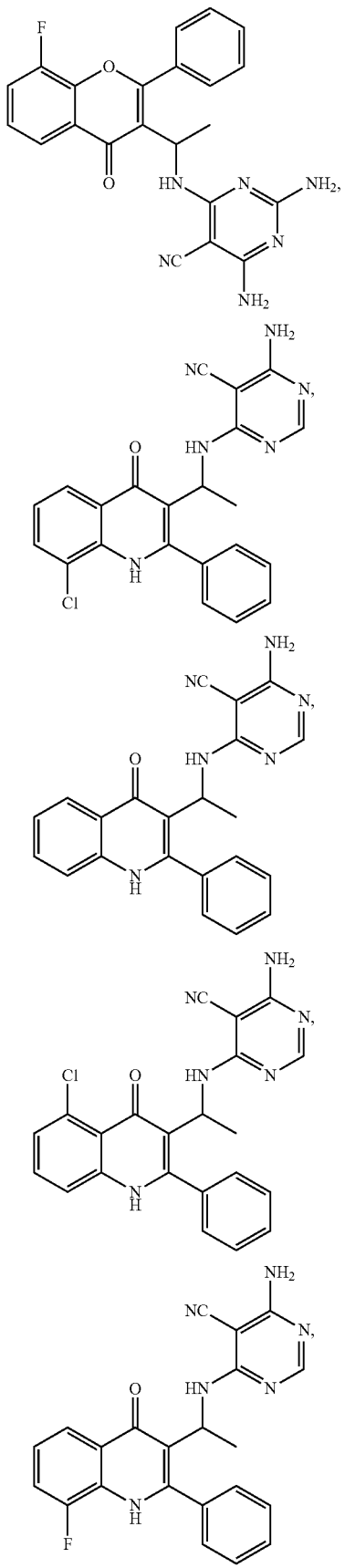

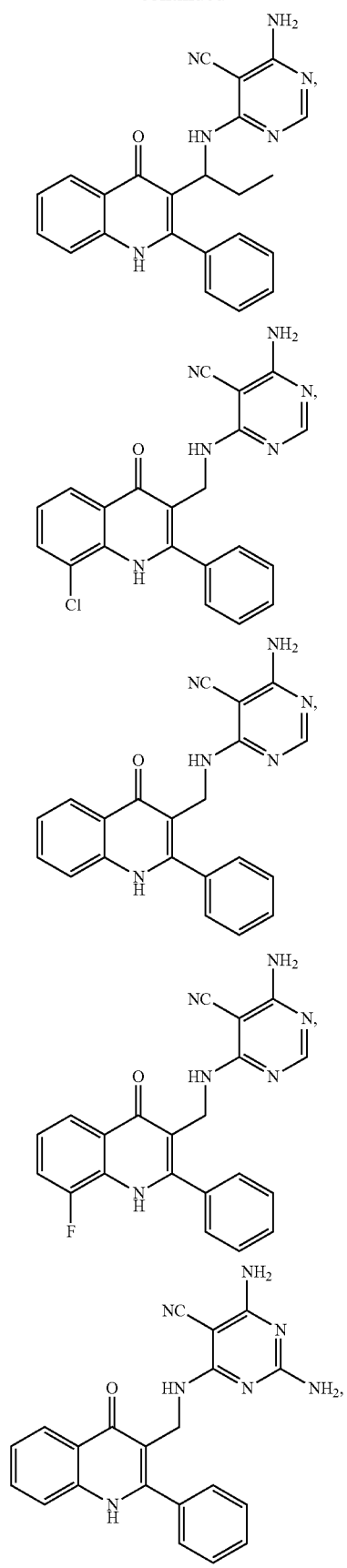
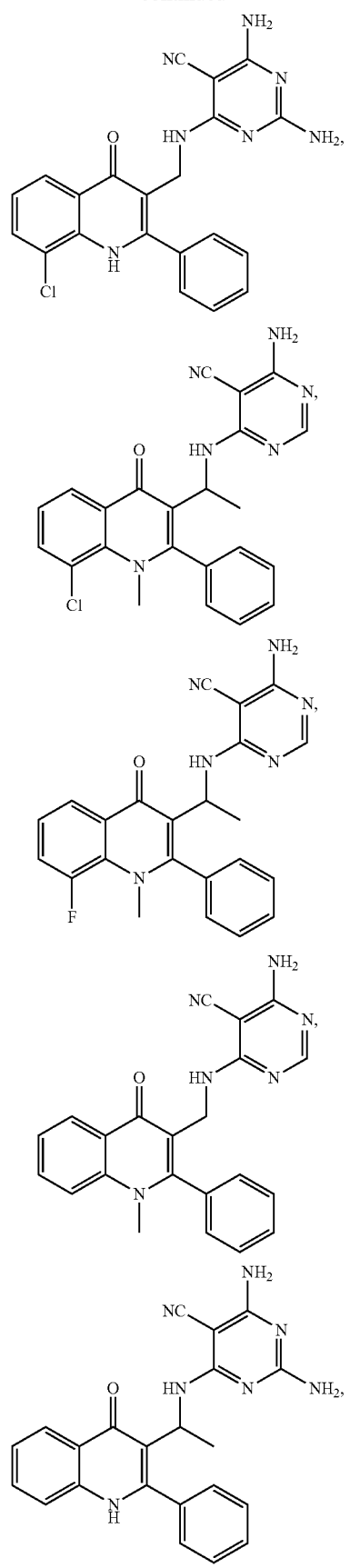

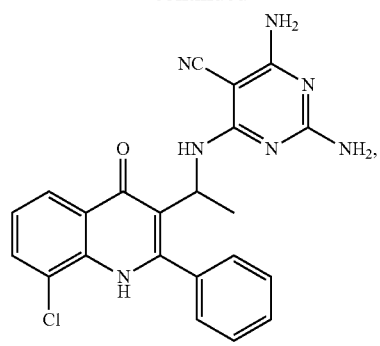
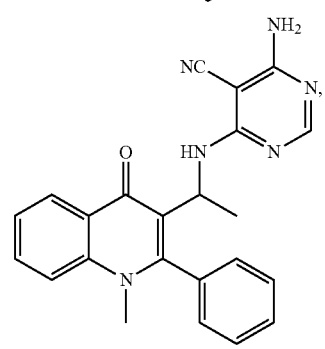
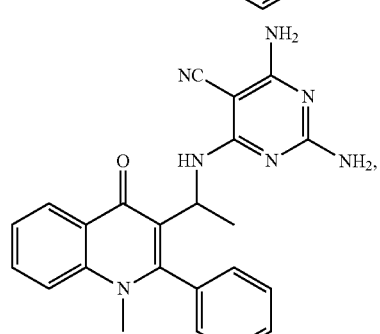
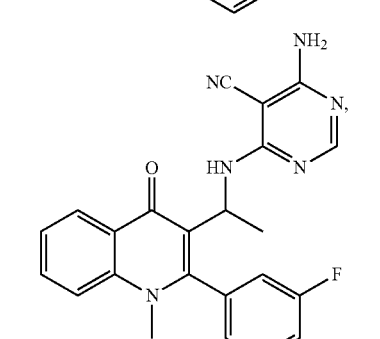
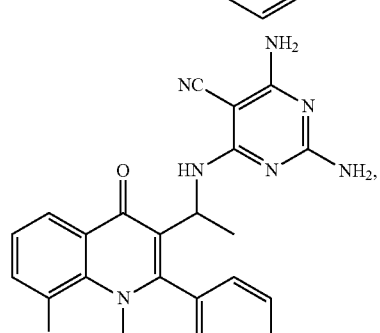
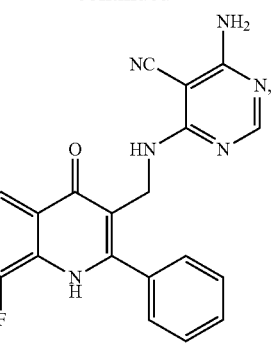
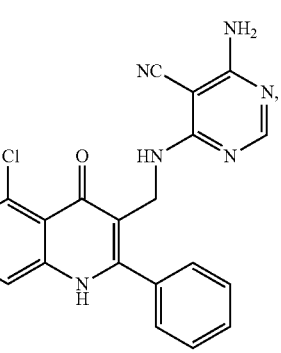
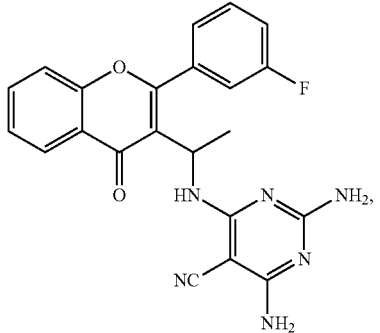
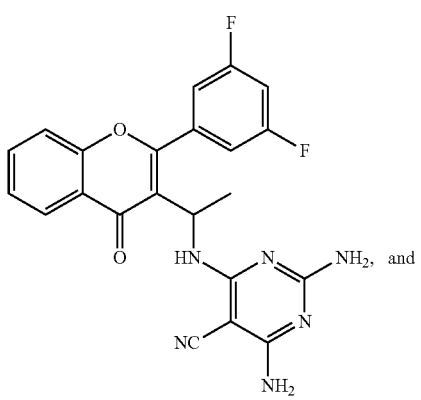

-continued

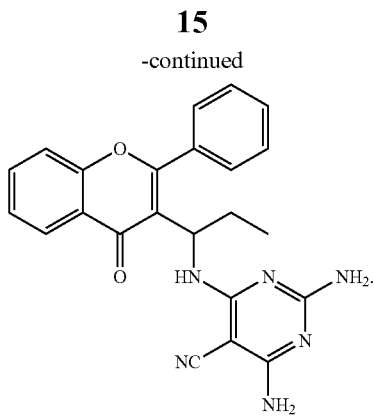

or a pharmaceutically acceptable salt thereof.

Another aspect of the present invention provides a method for preparing the compound of the general formula, comprising:

1. Preparation of the compound of formula I, in which Y is O:

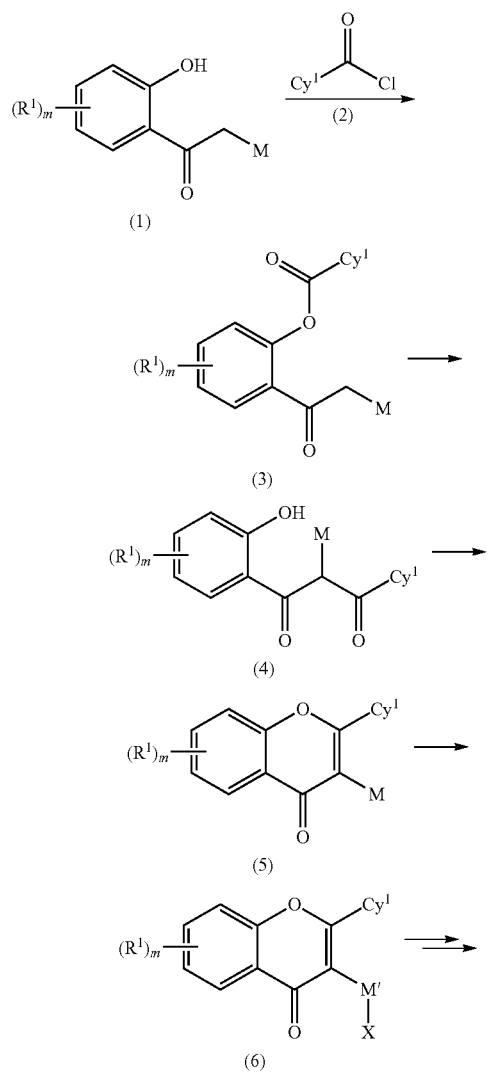

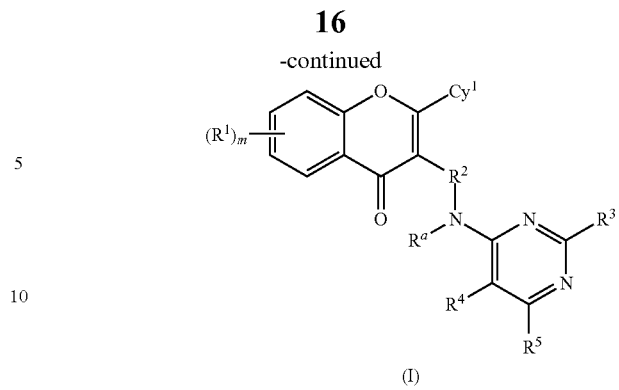

a) a compound of formula (1) is subjected to esterification reaction with a compound of formula (2) to give an intermediate of formula (3);

b) the intermediate of formula (3) is reacted with a strong base (such as sodium hydrogen) to give an intermediate of formula (4);

c) the intermediate of formula (4) is subjected to cyclization reaction under an acidic condition to give the intermediate of formula (5);

d) the intermediate of formula (5) is subjected to halogenation reaction to give the intermediate of formula (6);

e) the intermediate of formula (6) is subjected to a common reaction to give a compound of formula I.

Wherein, a common reaction in step e) includes but not limited to the following reactions: for example, the intermediate of formula (6) is subjected to ammonization reaction, followed by nucleophilic reaction with Y—$R^b$ to give a compound of formula (I); or the intermediate of formula (6) is subjected to esterification, hydrolysis and oxidation reactions, followed by reaction with tert-butylsulfenamide to give intermediate

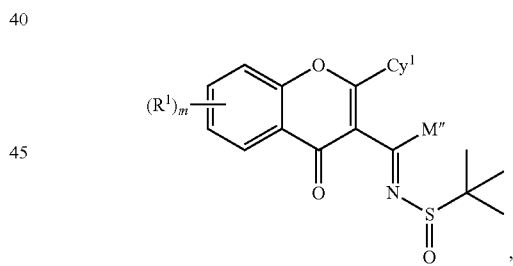

which then is reacted with an alkylating reagent and further subjected to nucleophilic reaction with Y—$R^b$ to give a compound of formula (I); or the intermediate of formula (6) is subjected to cyanidation and hydrolysis reactions, followed by condensation reaction with $NH_2$—$R^b$ to give a compound of formula (I).

Wherein, $Cy^1$, $R^2$, $R^3$, $R^4$, $R^5$ and m have the meaning as in formula I; $R^a$ represents hydrogen; M represents alkyl, preferably $C_{1-6}$ alkyl, more preferably $C_{1-3}$ alkyl; M' represents alkylene in which one H in M is substituted by X; M" represents the remaining residue after one carbon atom is removed from M, and when M is methyl, M" represents H; X and Y each independently represent halogen, preferably chlorine, bromine and iodine.

2. Preparation of compound of formula I, in which Y is N(R^b)

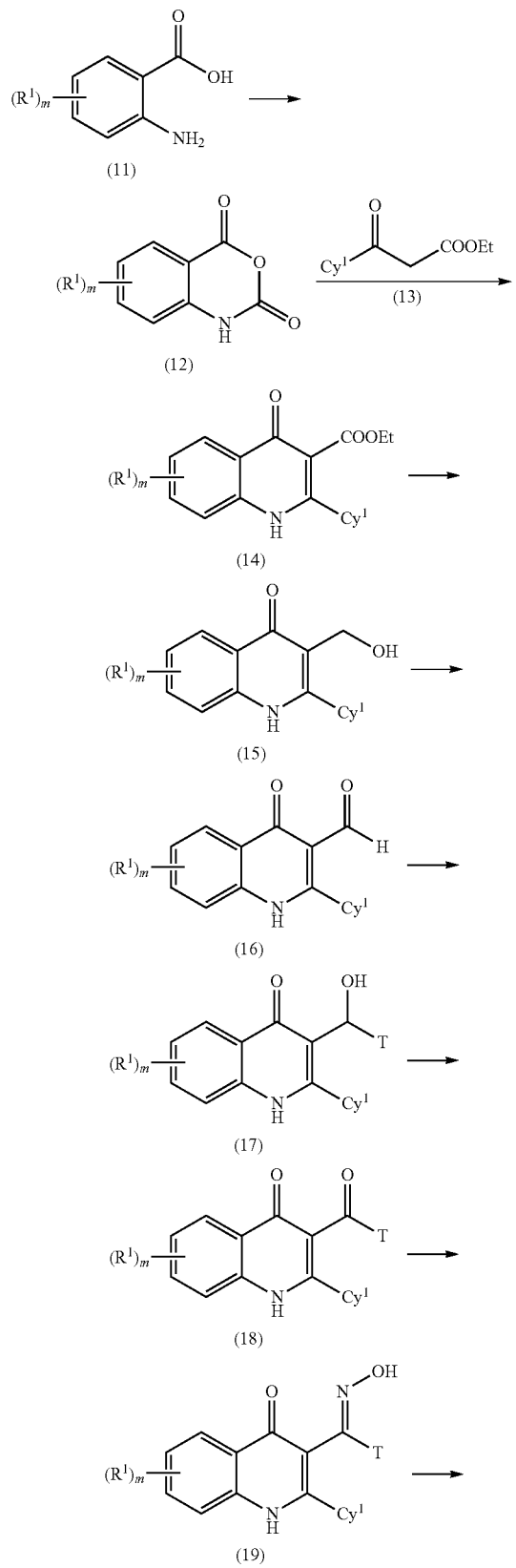

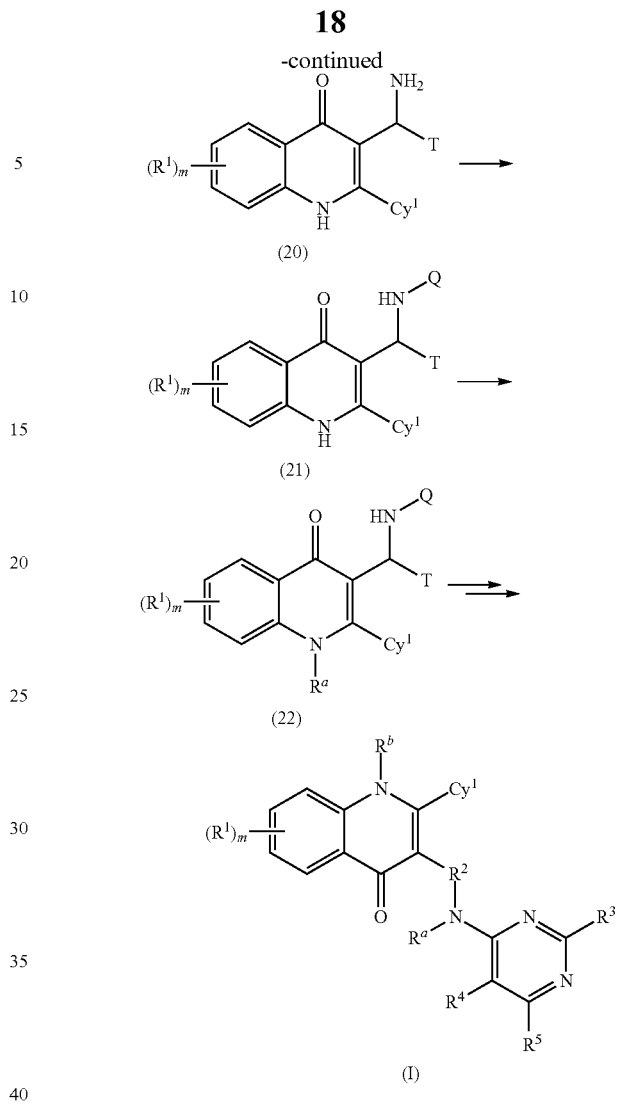

a') a compound of formula (11) is reacted with triphosgene to give an intermediate of formula (12);

b') the intermediate of formula (12) is reacted with a compound of formula (13) to give an intermediate of formula (14);

c') the intermediate of formula (14) is subjected to reduction reaction to give an intermediate of formula (15);

d') the intermediate of formula (15) is subjected to oxidation reaction to give an intermediate of formula (16);

e') the intermediate of formula (16) is reacted with an alkylating reagent to give an intermediate of formula (17);

f') the intermediate of formula (17) is subjected to oxidation reaction to give an intermediates of formula (18);

g') the intermediate of formula (18) is reacted with hydroxylamine to give an intermediate of formula (19);

h') the intermediate of formula (19) is subjected to reduction reaction to give an intermediate of formula (20);

i') the intermediate of formula (20) is reacted with an amino protecting group to give an intermediate of formula (21);

j') the intermediate of formula (21) is subjected to nucleophilic reaction with $R^b$—X to give an intermediate of formula (22);

k') after the amino protecting group is removed from the intermediate of formula (22), the intermediate of formula

(22) is subjected to conventional nucleophilic reactions to give a compound of formula I.

Wherein, $Cy^1$, $R^2$, $R^3$, $R^4$, $R^5$, m and $R^b$ have the meaning as in formula I; $R^a$ represents hydrogen; $R^2$ represents alkylene which is optionally further substituted with alkyl, and when $R^2$ represents methylene, the intermediate of formula (16) reacts directly with hydroxylamine, followed by step h'), i'), j') and k') to give a compound of formula I; T represents alkyl, preferably $C_{1-6}$ alkyl, and more preferably $C_{1-3}$ alkyl; X represents halogen, preferably chlorine, bromine and iodine.

In the third aspect, the present invention provides a pharmaceutical composition comprising the compound of the present invention or an isomer, pharmaceutically acceptable salt, solvate or prodrug thereof.

In some embodiments, a pharmaceutical composition provided in the present invention comprises the compound of the present invention or an isomer, pharmaceutically acceptable salt, solvate or prodrug thereof, and further comprises one or more of the following components: tyrosine protease inhibitors, EGFR inhibitors, VEGFR inhibitors, Bcr-Abl inhibitors, c-kit inhibitors, c-Met inhibitors, Raf inhibitors, MEK inhibitors, histone deacetylase inhibitors, VEGF antibody, EGF antibody, HIV protein kinase inhibitors, HMG-CoA reductase inhibitors and the like.

In some embodiments, the present invention provides a compound of the present invention or an isomer, pharmaceutically acceptable salt, solvate or prodrug thereof, and a pharmaceutical composition comprising the compound of the present invention or an isomer, pharmaceutically acceptable salt, solvate or prodrug thereof, wherein the compound or the pharmaceutical composition is used for the treatment and/or prevention of cancer, tissue proliferative disease or inflammatory disease.

The compound of the present invention or an isomer, pharmaceutically acceptable salt, solvate or prodrug thereof can be mixed with a pharmaceutically acceptable carrier, diluent or excipient to prepare a pharmaceutical preparation suitable for oral or parenteral administration. Methods of administration include, but are not limited to, intradermal, intramuscular, intraperitoneal, intravenous, subcutaneous, intranasal and oral routes. The preparations can be administered by any route, for example by infusion or bolus, by administration through an epithelial or mucocutaneous absorption (e.g., oral mucosa or rectum, etc.). The administration can be systemic or local. Examples of oral administration of the preparations include solid or liquid dosage forms, in particular, including tablets, pills, granules, powders, capsules, syrups, emulsions, suspensions and the like. The preparations can be prepared by methods known in the art and contain carriers, diluents or excipients conventionally used in the field of pharmaceutical preparation.

In the fourth aspect, the present invention provides a use of the compound of the present invention or an isomer, pharmaceutically acceptable salt, solvate or prodrug thereof, or the composition comprising the compound in the manufacture of a medicament for treatment and/or prevention of cancers, tissue proliferative diseases or inflammatory diseases. The cancer is selected from the group consisting of melanoma, papillary thyroid neoplasms, cholangiocarcinoma, colon cancer, ovarian cancer, lung cancer, malignant lymphoma, and cancer and sarcoma of liver, kidney, bladder, prostate, breast and pancreas, as well as primary and recurrent solid tumors of skin, colon, lung and ovarian or leukemia. The inflammatory disease is selected from the group consisting of allergy, asthma, rheumatoid arthritis, osteoarthritis, allergic conjunctivitis, allergic keratitis, dry eye, chronic obstructive pulmonary disease (COPD), lupus erythematosus, psoriasis, multiple sclerosis, end-stage renal disease, and the like.

In some embodiments, the present invention relates to a method for treating cancers, tissue proliferative diseases or inflammatory diseases, comprising administrating a patient in need thereof a therapeutically effective amount of the compound of formula (I) or an isomer, pharmaceutically acceptable salt, solvate or prodrug thereof, or a pharmaceutical composition comprising the compound. The cancer is selected from the group consisting of melanoma, papillary thyroid neoplasms, cholangiocarcinoma, colon cancer, ovarian cancer, lung cancer, malignant lymphoma, and cancer and sarcoma of liver, kidney, bladder, prostate, breast and pancreas, as well as primary and recurrent solid tumors of skin, colon, lung and ovarian or leukemia. The inflammatory diseases are selected from the group consisting of allergy, asthma, rheumatoid arthritis, osteoarthritis, allergic conjunctivitis, allergic keratitis, dry eye, chronic obstructive pulmonary disease (COPD), lupus erythematosus, psoriasis, multiple sclerosis, end-stage renal disease, and the like.

Terminologies

Unless there is a contrary statement, the terms used in the specification and the claims have the following meanings.

The "halogen" of the present invention refers to fluorine, chlorine, bromine and iodine.

The "alkyl" of the present invention refers to a straight or branched chain saturated aliphatic hydrocarbon group, preferably a straight or branched chain group having 1 to 6 carbon atoms, and further preferably straight or branched chain group containing 1 to 3 carbon atoms, non-limiting examples include methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl and the like. The alkyl can be substituted or unsubstituted, and when substituted, the substituent can be at any available connection point.

The "haloalkyl" of the present invention refers to an alkyl substituted with at least one halogen.

The "alkylene" of the present invention refers to a group in which one hydrogen atom is removed from alkyl, such as methylene (—$CH_2$—), ethylene (—$CH_2$—$CH_2$—), propylene (—$CH_2$—$CH_2$—$CH_2$—). As used herein, the "$C_{1-10}$ alkylene" refers to a group in which one hydrogen atom is removed from alkyl of $C_{1-10}$ alkyl; the "$C_{1-6}$ alkylene" refers to a group in which one hydrogen atom is removed from alkyl of $C_{1-6}$ alkyl.

The "alkenylene" of the present invention refers to a group in which one hydrogen atom is removed from alkenyl, such as ethenylene (—CH=CH—), propenylene (—CH=CH—$CH_2$— or —$CH_2$—CH=CH—), and the like. As used herein, the "$C_{2-10}$ alkenylene" refers to a group in which one hydrogen atom is removed from alkenyl of $C_{2-10}$ alkenyl; the "$C_{2-6}$ alkenylene" refers to a group in which one hydrogen atom is removed from alkenyl of $C_{2-6}$ alkenyl.

The "alkynylene" of the present invention refers to a group in which one hydrogen atom is removed from alkynyl, such as ethynylene (—C≡C—), propynylene (—C≡C—$CH_2$— or —$CH_2$—C≡C—), and the like. As used herein, the "$C_{2-10}$ alkynylene" refers to a group in which one hydrogen atom is removed from alkynyl of $C_{2-10}$ alkynyl; the "$C_{2-6}$ alkynylene" refers to a group in which one hydrogen atom is removed from alkynyl of $C_{2-6}$ alkynyl.

The "cycloalkyl" of the present invention refers to a cyclic saturated hydrocarbon. Favourable cycloalkyl can be substituted or unsubstituted monocyclic, bicyclic or tricyclic saturated hydrocarbon having 3 to 10 carbon atoms such as cyclopropyl, cyclobutyl, cyclopentyl, cyclohexyl.

The "heterocycloalkyl" of the present invention refers to a cyclic saturated hydrocarbon containing a heteroatom.

The "cycloalkylene" of the present invention refers to a group in which one hydrogen atom is removed from cycloalkyl, such as cyclopropylene

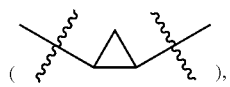

cyclobutylene

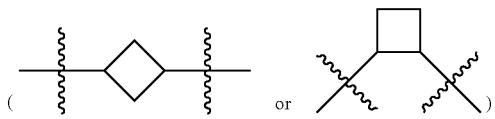 [SMILES: *C1CC(*)C1 ; *C1CCC1*]

and the like. As used herein, the "$C_{3-10}$ cycloalkylene" refers to a group in which one hydrogen atom is removed from cycloalkyl of $C_{3-10}$ cycloalkyl; the "$C_{3-6}$ cycloalkylene" refers to a group in which one hydrogen atom is removed from cycloalkyl of $C_{3-6}$ cycloalkyl.

The "alkoxy" of the present invention refers to —O-alkyl. Non-limiting examples of alkoxy include methoxy, ethoxy, propoxy, n-propoxy, isopropoxy, isobutoxy, sec-butoxy and the like. The alkoxy can be optionally substituted or unsubstituted, and when substituted, the substituent can be at any available connection point.

The "aryl" of the present invention refers to an aromatic system which may comprise a monocyclic or fused polycyclic ring, preferably aromatic system comprising a monocyclic or fused bicyclic ring containing 6 to 18 carbon atoms, preferably about 6 to about 14 carbon atoms. Favorable aryl includes, but is not limited to, phenyl, naphthyl, anthryl, tetrahydronaphthyl, fluorenyl, indanyl.

The "heteroaryl" in the present invention refers to an aryl group in which at least one carbon atom is replaced by a heteroatom, and the heteroatoms are O, S, N. Favorable heteroaryl includes, but is not limited to, imidazolyl, benzimidazolyl, imidazopyridyl, quinazolinonyl, pyrrolyl, imidazolonyl, furyl, thienyl, pyrazolyl, oxazolyl, thiazolyl, isoxazolyl, isothiazolyl, oxadiazolyl, triazolyl and the like. Herein, the "six to twelve-membered heteroaryl" in the present invention refers to a heteroaryl group consisting of 6 to 12 atoms and at least one atom is a heteroatom. Favorable six to twelve-membered heteroaryl includes, but is not limited to, pyrimidinyl, pyridyl, pyrazinyl, pyridazinyl, pyrimidopyrazolyl, pyrimidimidazolyl and the like.

The "solvate" of the present invention in the conventional sense refers to a complex formed by the combination of solutes (e.g., the active compound, the salt of the active compound) and a solvent (e.g., water). Solvents are the solvents known or readily known to those of ordinary skill in the art. In the case of water, solvates are commonly called hydrates, such as monohydrate, dihydrate, trihydrate and the like.

The "prodrug" of the present invention refers to a compound which is converted into the compound of formula (I) by reaction with an enzyme, a gastric acid or the like under physiological conditions in an organism, i.e., a compound is converted into the compound of formula (I) by oxidation, reduction, hydrolysis or the like of an enzyme, and/or a compound which is converted into the compound of formula (I) by hydrolysis reaction such as gastric acid or the like.

The "pharmaceutical composition" of the present invention refers to a mixture comprising any of the compounds described herein, including corresponding isomers, prodrugs, solvates, pharmaceutically acceptable salts or chemically protected forms thereof, and one or more pharmaceutically acceptable carriers. The purpose of the pharmaceutical compositions is to promote the administration of the compound to the organism. The compositions are commonly used to prepare pharmaceuticals for the treatment and/or prevention of diseases mediated by one or more kinases.

The "pharmaceutically acceptable carrier" of the present invention refers to a carrier which does not cause significant irritation to the organism and does not interfere with the biological activity and properties of the given compound, including all solvents, diluents or other excipients, dispersants, permeation enhancers such as surfactants, thickeners or emulsifiers, preservatives, solid binders, lubricants and the like. Unless any conventional carrier medium is incompatible with the compounds of the present invention. Some examples of pharmaceutically acceptable carriers include, but are not limited to, sugars such as lactose, glucose and sucrose; starches such as corn starch and potato starch; cellulose and derivatives thereof such as sodium carboxymethylcellulose, cellulose and cellulose acetate; malt, gelatin and so on.

The "excipient" of the present invention refers to an inert matter that is added to the pharmaceutical composition to further promote the administration of the compound. Excipients can include calcium carbonate, calcium phosphate, various sugars and various types of starches, cellulose derivatives, gelatin, vegetable oils and polyethylene glycols.

"Use in a medicament for the treatment and/or prevention of cancer, tissue proliferative disease or inflammatory disease" of the present invention refers to improving the cancers, tissue proliferative diseases or inflammatory diseases, inhibiting the growth, development and/or metastasis of cancer, or reducing the risk of cancers, tissue proliferative diseases or inflammatory diseases. It is mainly to administrate human or animal in need thereof a therapeutically or prophylactically effective amount of the compound of the present invention to inhibit, slow down or reverse the growth, development or spread of cancer in the subject, thus improving cancers, tissue proliferative diseases or inflammatory diseases, or reducing the risk of illness. The tumors include cancers, such as bladder cancer, breast cancer, kidney cancer, liver cancer, lung cancer (including small cell lung cancer), esophageal cancer, gallbladder cancer, ovarian cancer, pancreatic cancer, gastric cancer, cervical cancer, thyroid cancer, prostate cancer and skin cancer (including squamous cell carcinoma); lymphoid hematopoietic tumors, such as leukemia, acute lymphoblastic leukemia, acute lymphoblastic leukemia, B-cell lymphoma, T-cell lymphoma, Hodgkin's lymphoma, non-Hodgkin's lymphoma, hair cell lymphoma and Burkitt's lymphoma; mesenchymal cell-derived tumors, such as fibrosarcoma, rhabdomyosarcoma; myeloid hematopoietic tumors, such as acute and chronic myeloid leukemia, myelodysplastic syndrome and myeloid leukemia; central and peripheral nervous system tumors, such as astrocytomas, neuroblastomas, gliomas and schwannomas; and other tumors, such as melanoma, seminoma, teratocarcinoma, flesh tumor, color dry skin disease, keratoacanthoma, thyroid follicular carcinoma and Kaposi's sarcoma. The inflammatory diseases are selected from the group consisting of allergic reaction, asthma, rheumatoid arthritis, osteoarthritis, allergic conjunctivitis, allergic keratitis, dry eye, chronic obstructive pulmonary disease (COPD), lupus erythematosus, psoriasis, multiple sclerosis, end-stage renal disease, and the like.

The "pharmaceutically acceptable salts" of the present invention refers to salts of the compounds of the present invention which are safe and effective when using in mammals and have the desired biological activity.

DETAILED DESCRIPTION

The following representative embodiments are intended to better illustrate the invention and are not intended to limit the scope of the invention.

Example 1. 4-Amino-5-cyano-6-(4-oxo-2-phenyl-4H-chromen-3-yl) methylaminopyrimidine

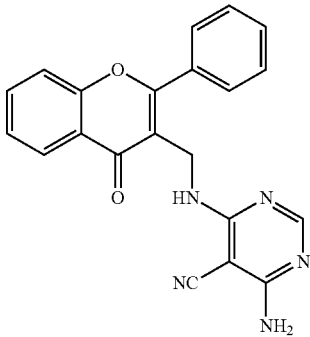 [SMILES: N#Cc1c(N)ncnc1NCc1c(-c2ccccc2)oc2ccccc2c1=O]

Step 1. Preparation of 2-Benzoyloxypropiophenone

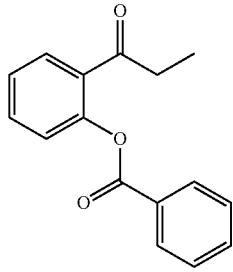 [SMILES: CCC(=O)c1ccccc1OC(=O)c1ccccc1]

2-Hydroxypropiophenone (5 g, 33.33 mmol), benzoyl chloride (11.7 g, 83.33 mmol) and potassium carbonate (23 g, 166.6 mmol) were added to 120 ml of acetone, heated to reflux in an oil bath and reacted overnight. TLC detection was performed until the completion of the reaction. After the completion of the reaction, the solvent was subjected to spin drying; water and ethyl acetate were added for extraction; extract was dried over anhydrous sodium sulfate and concentrated to give 6.5 g of an oil with a yield of 76.7%.

Step 2. Preparation of 3-Methyl-2-phenyl-4H-chromen-4-one

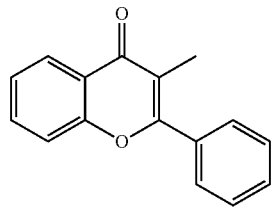 [SMILES: Cc1c(-c2ccccc2)oc2ccccc2c1=O]

2-Benzoyloxypropiophenone (6.5 g, 25.6 mmol) was dissolved in 80 ml of DMSO and cooled in an ice-water bath; sodium hydride (3.1 g, 76.7 mmol) was added in portions. Mixture was stirred at room temperature for about 2 h and TLC tracking was performed until the completion of the reaction. After completion of the reaction, water was added to the reaction solution, and the dilute hydrochloric acid was used to adjust the pH to a weak acidity. Mixture was extracted with ethyl acetate, dried over anhydrous sodium sulfate and concentrated to give an oil, that is, intermediate 1-(2-cyanophenyl)-2-methyl-3-phenyl-1,3-diacetone. 80 ml of acetic acid and several drops of concentrated hydrochloric acid were added to the oil and reaction was performed under reflux for about 3 h, followed by TLC tracking until the completion of the reaction. The reaction solution was subjected to spin drying and water was added, followed by extraction with water and ethyl acetate. Extract was dried over anhydrous sodium sulfate, concentrated and made into a mixture for chromatography, and purified by column chromatography to give 5 g of a white solid, yield: 82.7%.

Step 3. Preparation of 3-Bromomethyl-2-phenyl-4H-chromen-4-one

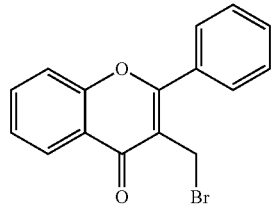 [SMILES: O=c1c(CBr)c(-c2ccccc2)oc2ccccc12]

3-Methyl-2-phenyl-4H-chromen-4-one (300 mg, 1.27 mmol), N-bromosuccinimide (NBS, 225 mg, 1.27 mmol) and benzoyl peroxide (BPO, 30 mg, 0.12 mmol) were dissolved in 15 ml of carbon tetrachloride, heated at reflux in an oil bath overnight. TLC tracking was performed until the completion of the reaction. Water was added to the reaction solution, and the reaction solution was extracted with ethyl acetate, dried over anhydrous sodium sulfate, concentrated and made into a mixture for chromatography, and purified by column chromatography to give 157 mg of white solid, yield: 39.4%.

Step 4. Preparation of 3-Aminomethyl-2-phenyl-4H-chromen-4-one hydrochloride

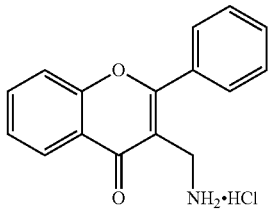

3-Bromomethyl-2-phenyl-4H-chromen-4-one (157 mg, 0.5 mmol) was dissolved in 5 ml of DMF; 2 ml of aqueous ammonia was added and stirred at room temperature overnight. TLC tracking was performed until the completion of the reaction. Water was added to the reaction solution, and the reaction solution was extracted with ethyl acetate, dried over anhydrous sodium sulfate until the organic layer was concentrated to about 5 ml. The saturated solution of hydrogen chloride in ethyl acetate was added and an off-white solid was gradually precipitated. Suction filter and drying were carried out to give 82 mg of product, yield: 57.1%.

Step 5. Preparation of 4-Amino-5-cyano-6-(4-oxo-2-phenyl-4H-chromen-3-yl) methylaminopyrimidine

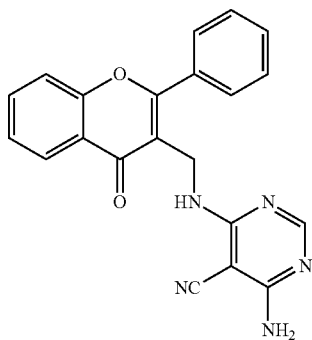 [SMILES: N#Cc1c(N)ncnc1NCc1c(-c2ccccc2)oc2ccccc2c1=O]

3-Aminomethyl-2-phenyl-4H-chromen-4-one hydrochloride (80 mg, 0.28 mmol), 4-amino-5-cyano-6-chloropyrimidine (47 mg, 0.30 mmol) and potassium carbonate (116 mg, 0.84 mmol) were dissolved in 3 ml of DMF and reacted at room temperature overnight. TLC tracking was performed until the completion of the reaction. Water was added to the reaction solution, and the reaction solution was extracted with ethyl acetate, dried over anhydrous sodium sulfate, concentrated and made into a mixture for chromatography, and purified by HPLC to give 12 mg of a white solid, yield: 11.6%.

$^1$H NMR (300 MHz, DMSO-$d_6$) δ: 8.13~8.12 (d, 1H, J=4.23 Hz), 7.94 (s, 1H), 7.85~7.82 (t, 1H, J=4.27 Hz), 7.74~7.72 (d, 2H, J=3.54 Hz), 7.69~7.67 (d, 1H, J=4.95 Hz), 7.57~7.52 (m, 4H), 7.23 (s, 1H), 7.18 (s, 2H), 4.40 (s, 2H). ES: m/z 370.1[M+H]$^+$.

Example 2. 2,4-Diamino-5-cyano-6-(4-oxo-2-phenyl-4H-chromen-3-yl) methylaminopyrimidine

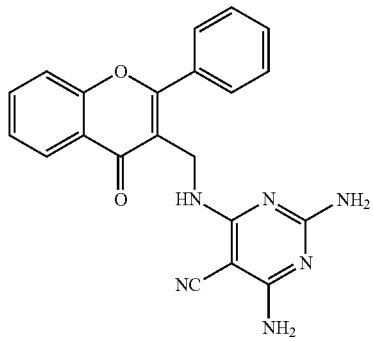 [SMILES: N#Cc1c(N)nc(N)nc1NCc1c(-c2ccccc2)oc2ccccc2c1=O]

3-Aminomethyl-2-phenyl-4H-chromen-4-one hydrochloride (100 mg, 0.34 mmol) of step 4 in Example 1, 2,4-diamino-5-cyano-6-chloropyrimidine (70 mg, 0.38 mmol) and potassium carbonate (140 mg, 1 mmol) were dissolved in 3 ml of DMF, heated in an oil bath at 100° C. and reacted overnight. TLC tracking was performed until the completion of the reaction. Water was added to the reaction solution, and the reaction solution was extracted with ethyl acetate, dried over anhydrous sodium sulfate, concentrated and made into a mixture for chromatography, and purified by HPLC to give 15 mg of a white solid, yield: 11.5%.

$^1$H NMR (300 MHz, DMSO-$d_6$) δ:8.14~8.11 (d, 1H, J=7.86 Hz), 7.86~7.82 (t, 1H, J=7.03 Hz), 7.76~7.73 (t, 2H, J=3.66 Hz), 7.69~7.67 (d, 1H, J=8.46 Hz), 7.59~7.51 (m, 4H), 6.65 (s, 1H), 6.49 (s, 2H), 6.22 (s, 2H), 4.32~4.30 (d, 2H, J=3.69 Hz). ES: m/z 385.0[M+H]$^+$.

Example 3. Preparation of 4-Amino-5-cyano-6-(1-(4-oxo-2-phenyl-4H-chromen-3-yl) ethylamino) pyrimidine

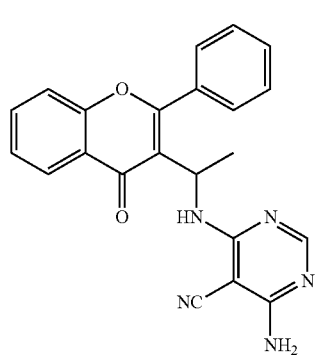 [SMILES: CC(Nc1ncnc(N)c1C#N)c1c(-c2ccccc2)oc2ccccc2c1=O]

Step 1. Preparation of 3-Acetoxymethyl-2-phenyl-4H-chromen-4-one

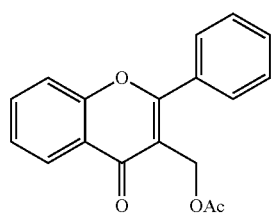 [SMILES: CC(=O)OCc1c(-c2ccccc2)oc2ccccc2c1=O]

3-Bromomethyl-2-phenyl-4H-chromen-4-one (33.1 g, 0.105 mol) in step 3 of Example 1 and sodium acetate (43 g, 0.527 mol) were dissolved in 700 ml DMF, placed in oil bath and heated to 75° C., and reacted for 4 h. TLC tracking was performed until the completion of the reaction. Reaction solution was poured into water slowly and solid was precipitated. After suction filtration, wet product was used directly to the next step.

Step 2. Preparation of 3-Hydroxymethyl-2-phenyl-4H-chromen-4-one

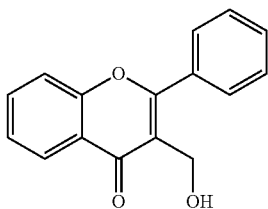 [SMILES: O=c1c(CO)c(-c2ccccc2)oc2ccccc12]

The wet product of step 1 was added to 530 ml of THF and 200 ml of water, and sodium hydroxide (12.65 g, 0.315 mol) was added. Reaction was carried out at room temperature overnight and TLC tracking was performed until the completion of the reaction. The main portion of THF was removed by spin drying. Yellow solid was precipitated, suction filtered and dried to give 22.1 g of solid. Yield of two steps was 83.5%.

Step 3. Preparation of 3-Formyl-2-phenyl-4H-chromen-4-one

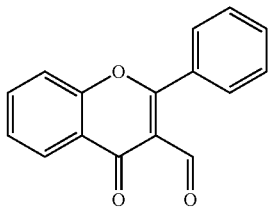 [SMILES: O=Cc1c(-c2ccccc2)oc2ccccc2c1=O]

3-Hydroxymethyl-2-phenyl-4H-chromen-4-one (22.1 g, 87.7 mmol) and o-iodo benzoic acid (IBX, 27 g, 96.4 mmol) were dissolved in 500 ml DMSO and reacted at room temperature overnight. TLC tracking was performed until the completion of the reaction. The reaction solution was poured into a large amount of water to precipitate a white solid. The solid was added to the water, extracted with ethyl acetate, dried over anhydrous sodium sulfate and subjected to spin drying to give 15.2 g of a yellowish white solid with a yield of 68.7%.

Step 4. Preparation of 2-Methyl-N-((4-oxo-2-phenyl-4H-chromen-3-yl) methylene) propane-2-sulfenamide

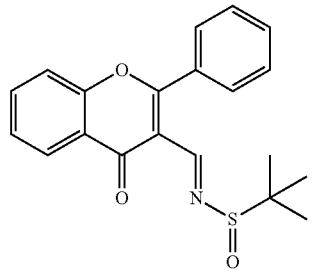 [SMILES: CC(C)(C)S(=O)/N=C/c1c(-c2ccccc2)oc2ccccc2c1=O]

3-Formyl-2-phenyl-4H-chromen-4-one (1 g, 4 mmol), tert-butylsulfenamide (0.53 g, 4.4 mmol) and cesium carbonate (1.95 g, 6 mmol) were dissolved in 25 ml DCM. Reaction was carried out at room temperature overnight and TLC tracking was performed until the completion of the reaction. The reaction solution was subjected to spin drying, extracted with ethyl acetate, dried over anhydrous sodium sulfate and subjected to spin drying to give 0.8 g of a yellowish white solid with a yield of 56.6%.

Step 5. Preparation of 3-(1-Aminoethyl)-2-phenyl-4H-chromen-4-one hydrochloride

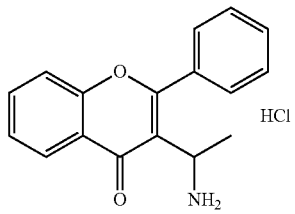 [SMILES: CC(N)c1c(-c2ccccc2)oc2ccccc2c1=O ; Cl]

2-Methyl-N-((4-oxo-2-phenyl-4H-chromen-3-yl) methylene) propane-2-sulfenamide (5.3 g, 15 mmol) was dissolved in 60 ml THF, replaced with argon three times and cooled in −20° C. cold trap. THF solution of methyl magnesium chloride (10 ml, 30 mmol) was added and reacted in cool trap for 2 h. TLC tracking was performed until the completion of the reaction. The reaction solution was quenched by ammonium chloride aqueous solution, extracted with ethyl acetate, dried over anhydrous sodium sulfate and subjected to spin drying to give an oil. The oil was dissolved in a small amount of ethyl acetate, solution of hydrogen chloride in ethyl acetate was added and grey solid was gradually precipitated. After stirring for a moment, the grey solid was subjected to suction filtration and dried to give 3.8 g of solid. The yield of two steps was 84.2%.

Step 6. Preparation of 4-Amino-5-cyano-6-(1-(4-oxo-2-phenyl-4H-chromen-3-yl) ethylamino) pyrimidine

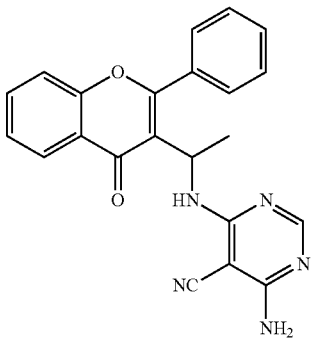 [SMILES: CC(Nc1ncnc(N)c1C#N)c1c(-c2ccccc2)oc2ccccc2c1=O]

3-(1-Aminoethyl)-2-phenyl-4H-chromen-4-one hydrochloride (700 mg, 3.32 mmol), 4-amino-5-cyano-6-chloropyrimidine (716 mg, 4.65 mmol) and potassium carbonate (1.6 g, 11.62 mmol) were dissolved in 20 ml DMF and reacted in a 100° C. oil bath for 24 h. TLC tracking was performed until the completion of the reaction. Water was added to the reaction solution, and the reaction solution was extracted with ethyl acetate, dried over anhydrous sodium sulfate, subjected to spin drying and made into a mixture for chromatography, and separated by column chromatography to give 200 mg of a white solid with a yield of 52.2%.

$^1$H NMR (300 MHz, DMSO-d$_6$) δ: 8.18~8.15 (d, 1H, J=7.5 Hz), 7.91 (s, 1H), 7.87~7.82 (t, 1H, J=7.6 Hz), 7.71~7.67 (m, 2H), 7.63 (s, 4H), 7.57~7.52 (t, 1H, J=7.9 Hz), 7.30 (s, 3H), 5.39~5.35 (t, 1H, J=6.9 Hz), 1.50~1.48 (d, 3H, J=6.6 Hz). ES: m/z 383.9[M+H]$^+$.

Example 4. 2,4-Diamino-5-cyano-6-(1-(4-oxo-2-phenyl-4H-chromen-3-yl) ethylamino) pyrimidine

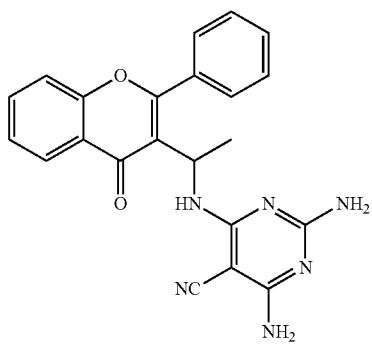 [SMILES: CC(Nc1nc(N)nc(N)c1C#N)c1c(-c2ccccc2)oc2ccccc2c1=O]

3-(1-Aminoethyl)-2-phenyl-4H-chromen-4-one hydrochloride (700 mg, 3.32 mmol) obtained in step 5 of Example 3, 2,4-diamino-5-cyano-6-chloropyrimidine (716 mg, 4.65 mmol) and potassium carbonate (1.6 g, 11.62 mmol) were dissolved in 20 ml DMF and reacted in a 100° C. oil bath for 24 h. TLC tracking was performed until the completion of the reaction. Water was added to the reaction solution, and the reaction solution was extracted with ethyl acetate, dried over anhydrous sodium sulfate, subjected to spin drying and made into a mixture for chromatography, and separated by column chromatography to give 20 mg of a white solid with a yield of 5.2%.

$^1$H NMR (300 MHz, DMSO-d$_6$) δ: 8.16~8.15 (d, 1H, J=4.2 Hz), 7.86~7.83 (t, 1H, J=4.6 Hz), 7.73~7.72 (m, 2H), 7.66~7.63 (m, 4H), 7.56~7.53 (t, 1H, J=4.5 Hz), 6.92~6.90 (d, 1H, J=5.5 Hz), 6.57 (s, 2H), 6.00 (br, 2H), 5.40~5.34 (m, 1H), 1.44~1.43 (d, 3H, J=4.1 Hz). ES: m/z 399.0 [M+H]$^+$.

Example 5. 4-Amino-5-cyano-6-(1-(8-chloro-4-oxo-2-phenyl-4H-chromen-3-yl) ethylamino) pyrimidine

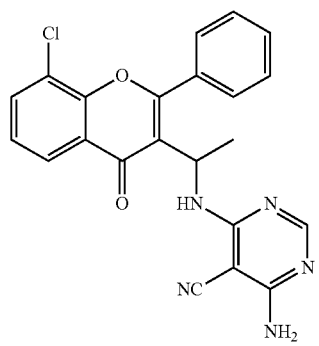 [SMILES: CC(Nc1ncnc(N)c1C#N)c1c(-c2ccccc2)oc2c(Cl)cccc2c1=O]

Step 1. Preparation of 3-bromomethyl-8-chloro-2-phenyl-4H-chromen-4-one

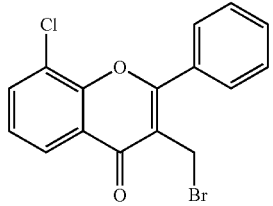 [SMILES: O=c1c(CBr)c(-c2ccccc2)oc2c(Cl)cccc12]

The preparation method was the same as the method for preparing 3-bromomethyl-2-phenyl-4H-chromen-4-one of steps 1~3 in Example 1, except that 2-hydroxypropiophenone in the materials was replaced with 2-hydroxy-3-chloropropiophenone.

Step 2. Preparation of 3-(1-Aminoethyl)-8-chloro-2-phenyl-4H-chromen-4-one hydrochloride

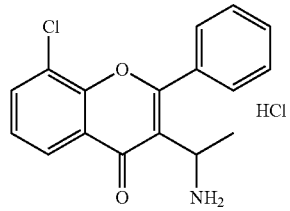 [SMILES: CC(N)c1c(-c2ccccc2)oc2c(Cl)cccc2c1=O ; Cl]

The preparation method was the same as the method for preparing 3-(1-aminoethyl)-2-phenyl-4H-chromen-4-one hydrochloride of steps 1~5 in Example 3, except that 3-bromomethyl-2-phenyl-4H-chromen-4-one in the materials was replaced with 3-bromomethyl-8-chloro-2-phenyl-4H-chromen-4-one.

Step 3. Preparation of 4-Amino-5-cyano-6-(1-(8-chloro-4-oxo-2-phenyl-4H-chromen-3-yl) ethylamino) pyrimidine 3-(1-Aminoethyl)-8-chloro-2-phenyl-4H-chromen-4-one hydrochloride (200 mg, 0.59 mmol), 4-amino-5-cyano-6-chloropyrimidine (101 mg, 0.65 mmol) and potassium carbonate (244 mg, 1.77 mmol) were dissolved in 20 ml DMF and reacted in a 100° C. oil bath for 24 h. TLC tracking was performed until the completion of the reaction. Water was added to the reaction solution, and the reaction solution was extracted with ethyl acetate, dried over anhydrous sodium sulfate, subjected to spin drying and made into a mixture for chromatography, and separated by column chromatography to give 35 mg of a white solid, yield: 14.2%.

$^1$H NMR (300 MHz, DMSO-d$_6$) δ: 8.12~8.10 (d, 1H, J=7.8 Hz), 8.03~8.00 (d, 1H, J=7.8 Hz), 7.92 (s, 1H), 7.76~7.74 (m, 2H), 7.65 (s, 3H), 7.56~7.51 (t, 1H, J=7.9 Hz), 7.30 (s, 2H), 7.20~7.17 (d, 1H, J=8.6 Hz), 5.44~5.36 (m, 1H), 1.52~1.50 (d, 3H, J=6.8 Hz). ES: m/z 418.1 [M+H]$^+$.

Example 6. 2,4-Diamino-5-cyano-6-(1-(8-chloro-4-oxo-2-phenyl-4H-chromen-3-yl) ethylamino)pyrimidine

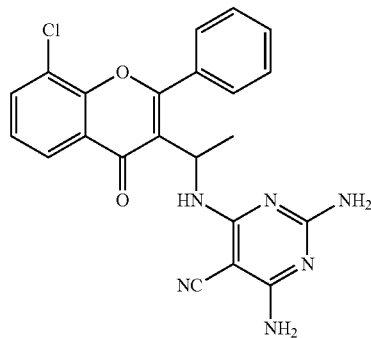 [SMILES: CC(Nc1nc(N)nc(N)c1C#N)c1c(-c2ccccc2)oc2c(Cl)cccc2c1=O]

3-(1-Aminoethyl)-8-chloro-2-phenyl-4H-chromen-4-one hydrochloride (200 mg, 0.59 mmol) obtained in step 2 of Example 5, 2,4-diamino-5-cyano-6-chloropyrimidine (101 mg, 0.65 mmol) and potassium carbonate (244 mg, 1.77 mmol) were dissolved in 20 ml DMF and reacted in a 100° C. oil bath for 24 h. TLC tracking was performed until the completion of the reaction. Water was added to the reaction solution, and the reaction solution was extracted with ethyl acetate, dried over anhydrous sodium sulfate, subjected to spin drying and made into a mixture for chromatography, and separated by column chromatography to give 23 mg of a white solid with a yield of 9.0%.

$^1$H NMR (300 MHz, DMSO-d$_6$) δ: 8.12~8.09 (d, 1H, J=7.2 Hz), 8.03~8.01 (d, 1H, J=7.6 Hz), 7.76~7.75 (d, 2H, J=2.8 Hz), 7.67~7.66 (d, 3H, J=2.3 Hz), 7.56~7.50 (t, 1H, J=7.9 Hz), 6.84~6.81 (d, 1H, J=9.0 Hz), 6.60 (s, 2H), 6.12 (br, 2H), 5.47~5.39 (m, 1H), 1.45~1.43 (d, 3H, J=6.8 Hz). ES: m/z 433.2[M+H]$^+$.

Example 7. 4-Amino-5-cyano-6-(1-(8-fluoro-4-oxo-2-phenyl-4H-chromen-3-yl) ethylamino) pyrimidine

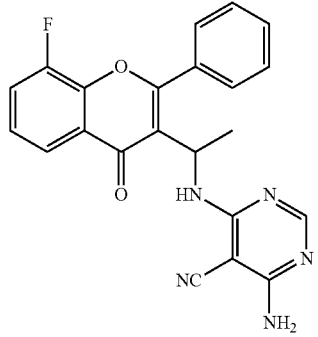 [SMILES: CC(Nc1ncnc(N)c1C#N)c1c(-c2ccccc2)oc2c(F)cccc2c1=O]

Step 1. Preparation of 3-(1-Aminoethyl)-8-fluoro-2-phenyl-4H-chromen-4-one hydrochloride The preparation method was the same as the method for preparing 3-(1-aminoethyl)-8-chloro-2-phenyl-4H-chromen-4-one hydrochloride of steps 1~2 in Example 5, except that 2-hydroxy-3-chloropropiophenone in the materials was replaced with 2-hydroxy-3-fluoropropiophenone.

Step 2. Preparation of 4-Amino-5-cyano-6-(1-(8-fluoro-4-oxo-2-phenyl-4H-chromen-3-yl) ethylamino) pyrimidine 3-(1-Aminoethyl)-8-fluoro-2-phenyl-4H-chromen-4-one hydrochloride (200 mg, 0.59 mmol), 4-amino-5-cyano-6-chloropyrimidine (101 mg, 0.65 mmol) and potassium carbonate (244 mg, 1.77 mmol) were dissolved in 20 ml DMF and reacted in a 100° C. oil bath for 24 h. TLC tracking was performed until the completion of the reaction. Water was added to the reaction solution, and the reaction solution was extracted with ethyl acetate, dried over anhydrous sodium sulfate, subjected to spin drying and made into a mixture for chromatography, and separated by column chromatography to give 51 mg of a white solid with a yield of 21.5%.

$^1$H NMR (300 MHz, DMSO-d$_6$) δ: 7.97~7.92 (m, 2H), 7.85~7.78 (t, 1H, J=9.5 Hz), 7.74~7.72 (m, 2H), 7.64~7.63 (m, 3H), 7.55~7.51 (m, 1H), 7.32 (s, 2H), 7.20~7.17 (d, 1H, J=8.3 Hz), 5.43~5.35 (m, 1H), 1.52~1.49 (d, 3H, J=6.8 Hz). ES: m/z 402.1[M+H]$^+$.

Example 8. 2,4-Diamino-5-cyano-6-(1-(8-fluoro-4-oxo-2-phenyl-4H-chromen-3-yl) ethylamino) pyrimidine

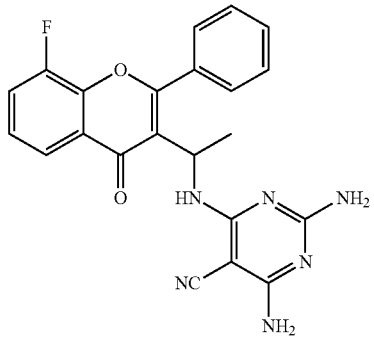 [SMILES: CC(Nc1nc(N)nc(N)c1C#N)c1c(-c2ccccc2)oc2c(F)cccc2c1=O]

3-(1-Aminoethyl)-8-fluoro-2-phenyl-4H-chromen-4-one hydrochloride (190 mg, 0.59 mmol) obtained in step 1 of Example 7, 2,4-diamino-5-cyano-6-chloropyrimidine (101 mg, 0.65 mmol) and potassium carbonate (244 mg, 1.77 mmol) were dissolved in 20 ml DMF and reacted in a 100° C. oil bath for 24 h. TLC tracking was performed until the completion of the reaction. Water was added to the reaction solution, and the reaction solution was extracted with ethyl acetate, dried over anhydrous sodium sulfate, subjected to spin drying and made into a mixture for chromatography, and separated by column chromatography to give 32 mg of a white solid with a yield of 13.0%.

$^1$H NMR (300 MHz, DMSO-$d_6$) δ: 7.92~7.88 (m, 2H), 7.85~7.75 (m, 2H), 7.70~7.65 (m, 2H), 7.61~7.56 (m, 3H), 7.50~7.46 (m, 1H), 7.27 (s, 2H), 7.17~7.13 (d, 1H, J=8.0 Hz), 5.40~5.32 (m, 1H), 1.55~1.50 (d, 3H, J=6.6 Hz). ES: m/z 417.1[M+H]$^+$.

Example 9. 4-Amino-5-cyano-6-((1-(8-chloro-4-oxo-2-phenyl-1,4-dihydroquinolin-3-yl)ethyl)amino) pyrimidine

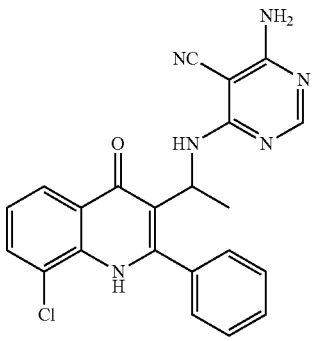 [SMILES: CC(Nc1ncnc(N)c1C#N)c1c(-c2ccccc2)[nH]c2c(Cl)cccc2c1=O]

Step 1. Preparation of 3-Chloroisatoic anhydride

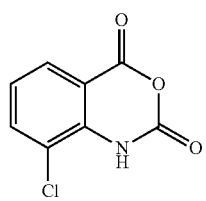 [SMILES: O=c1[nH]c2c(Cl)cccc2c(=O)o1]

2-Amino-3-chlorobenzoic acid (34.2 g, 0.2 mol) and 175 ml of acetonitrile were added to a 500 ml three-necked flask, heated to 55° C., and then triphosgene in dichloromethane (triphosgene (29.6 g, 0.1 mol) dissolved in 150 ml of dichloromethane) was added dropwise, and pyridine (50 ml, 0.6 mol) was added dropwise at the same time, the dropping was completed in about 30 min, and the reaction was carried out for 5 h. TLC tracking was performed until the completion of the reaction. The reaction solution was subjected to suction filtration when it was still hot, and the filter cake was washed with 100 ml ethyl acetate. The solvent was removed from the filtrate to give a black oil. Ice-water mixture was added to the black oil and a large amount of solid was precipitated. The solid was subjected to suction filtration, drying, recrystallization by ethyl acetate-petroleum ether system, and then subjected to suction filtration and drying to give 30.8 g of grey solid with a yield of 78.2%.

Step 2. Preparation of Ethyl 8-chloro-4-oxo-2-phenyl-1,4-dihydroquinoline-3-formate

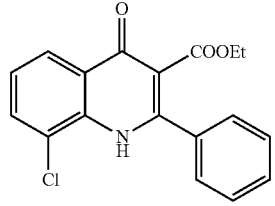 [SMILES: CCOC(=O)c1c(-c2ccccc2)[nH]c2c(Cl)cccc2c1=O]

Ethyl benzoylacetate (19.2 g, 0.1 mol) and 50 ml of DMF were added to a 250 ml three-necked flask and cooled to −20° C. Then 60% NaH (4.0 g, 0.1 mol) was added in portions and there were a lot of bubbles coming out. The temperature was kept not exceeding 0° C. and the reaction was completed in about 30 min. The solution was continued stirring for 15 min and the temperature was warmed up to room temperature. The solution was stand-by with stirring. 3-Chloroisatoic anhydride (19.7 g, 0.1 mol) was dissolved in 100 ml of DMF and added dropwise to the above reaction solution through a constant pressure dropping funnel. The reaction system was kept in a condition of anhydrous and oxygen free. After 30 min, dropping was completed; the reaction solution was heated to 150° C. and stirred. TLC tracking was performed until the completion of the reaction. The solvent was removed from the reaction solution under reduced pressure to give a black oil. Ice-water mixture was added and extraction was performed with ethyl acetate. The organic layers were combined and subjected to drying, removal of the solvent, made into a mixture for chromatography and separated by column chromatography to give 18.3 g of a pale yellow solid with a yield of 55.9%.

Step 3. Preparation of 8-Chloro-3-hydroxymethyl-2-phenylquinolin-4-(1H)-one

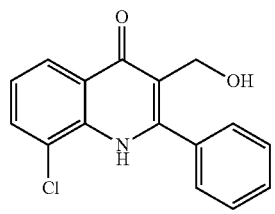 [SMILES: O=c1c(CO)c(-c2ccccc2)[nH]c2c(Cl)cccc12]

Ethyl 8-chloro-4-oxo-2-phenyl-1,4-dihydroquinoline-3-formate (16.4 g, 0.05 mol) and 100 ml THF were added to a 250 ml three-necked flask, stirred to be dissolved and cooled to −20° C. Lithium aluminum hydride (3.8 g, 0.1 mol) was added in portions and there were bubbles coming out. The speed was controlled, the temperature was maintained below or equal to 0° C., and the adding was completed in about 15 min. The temperature was raised to room temperature and stirring was carried out for 2 h. TLC tracking was performed until the completion of the reaction. After the reaction was stopped, 3.8 g sodium sulfate decahydrate was added in portions and there were bubbles coming out. The adding speed was controlled to avoid washing away the materials. After adding, reaction was carried out at room temperature with stirring for 0.5 h. Suction filtration was performed, solid was washed with tetrahydrofuran 3 times, solvent was removed and spin drying was performed to give 12.7 g of a solid with a yield of 88.6%.

Step 4. Preparation of 8-chloro-4-oxo-2-phenyl-1,4-dihydroquinoline-3-carbaldehyde

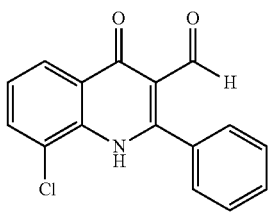 [SMILES: O=Cc1c(-c2ccccc2)[nH]c2c(Cl)cccc2c1=O]

8-Chloro-3-hydroxymethyl-2-phenylquinolin-4-(1H)-one (11.4 g, 0.04 mol) and 100 ml of DMSO were added to a 250 ml three-necked flask and stirred to be dissolved. IBX (14 g, 0.05 mol) was then added, temperature was raised to 35° C. and mixture was stirred for 5 h. TLC tracking was performed until the completion of the reaction. The reaction was stopped, 300 ml of ethyl acetate was added, temperature was raised to reflux and reaction was carried out for 15 min. Suction filtration was performed while the mixture was hot. The solid was washed with hot ethyl acetate 3 times, filtrates were combined, 200 ml water was added. After stratification, aqueous layer was extracted with ethyl acetate, and the organic layers were combined, washed with saturated salt water, dried over anhydrous sodium sulfate, and solvent was distilled off under reduced pressure to give 9.9 g of a light yellow solid with a yield of 87.5%.

Step 5. Preparation of 8-Chloro-3-(1-hydroxyethyl)-2-phenylquinolin-4(1H)-one

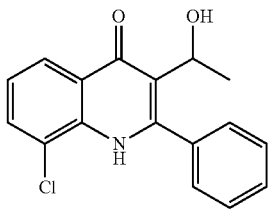

8-Chloro-4-oxo-2-phenyl-1,4-dihydroquinoline-3-carbaldehyde (8.5 g, 0.03 mol) and 50 ml of anhydrous tetrahydrofuran were added to a 100 ml two-necked flask, stirred to be dissolved, cooled to −35° C. and protected with argon. A solution of methylmagnesium chloride in tetrahydrofuran (concentration of 3M) (3 ml, 0.09 mol) was added via syringe. After adding, the temperature was raised to 0° C. and the mixture was stirred for 2 h. TLC tracking was performed until the completion of the reaction. The reaction was stopped; 5 ml ethanol was added to quench the reaction; the solvent was evaporated under reduced pressure; 200 ml of water and 100 ml of ethyl acetate were added. After stratification, aqueous layer was extracted with ethyl acetate, and the organic layers were combined, washed with saturated salt water, dried over anhydrous sodium sulfate, and concentrated under reduced pressure to give 8.2 g of a light yellow solid with a yield of 91.2%.

Step 6. Preparation of 3-Acetyl-8-chloro-2-phenylquinolin-4(1H)-one

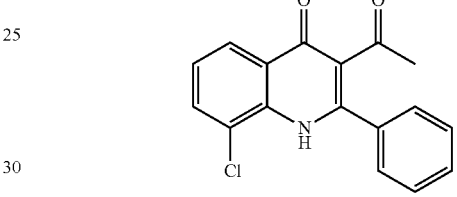

8-Chloro-3-(1-hydroxyethyl)-2-phenylquinolin-4(1H)-one (6 g, 0.02 mol) and 60 ml of DMSO were added to a 100 ml three-necked flask and stirred to be dissolved. IBX (8.4 g, 0.03 mol) was then added; temperature was raised to 35° C. and mixture was stirred for 5 h. TLC tracking was performed until the completion of the reaction. The reaction was stopped, 300 ml of ethyl acetate was added, temperature was raised and reaction was carried out under reflux for 15 min. Suction filtration was performed while the mixture was hot. The solid was washed with hot ethyl acetate 3 times, filtrates were combined and 200 ml water was added. After stratification, aqueous layer was extracted with ethyl acetate, and the organic layers were combined, washed with saturated salt water, dried over anhydrous sodium sulfate, and solvent was evaporated under reduced pressure to give 5.4 g of a light yellow solid with a yield of 90.2%.

Step 7. Preparation of 8-Chloro-3-(1-(hydroxyimino)ethyl)-2-phenylquinolin-4 (1H)-one

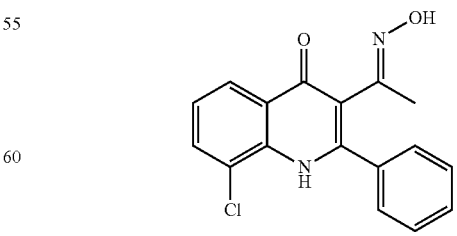

3-Acetyl-8-chloro-2-phenylquinolin-4(1H)-one (4.5 g, 0.015 mol) and 50 ml of anhydrous methanol were added to a 100 ml three-necked flask and stirred to be dissolved.

Hydroxylamine hydrochloride (6.3 g, 0.09 mol) and sodium acetate (9.8 g, 0.12 mol) were then added; temperature was raised to 45° C. and mixture was stirred for 5 h. TLC tracking was performed until the completion of the reaction. The reaction was stopped; solvent was removed under reduced pressure and 100 ml water was added to the residue. A large amount of light yellow solid was precipitated and subjected to suction filtration and water washing. The filter cake was dried to give 4.8 g of a light yellow solid with a yield of 87.1%.

Step 8. Preparation of 3-(1-Aminoethyl)-8-chloro-2-phenylquinolin-4(1H)-one

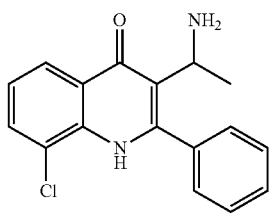

8-Chloro-3-(1-(hydroxyimino)ethyl)-2-phenylquinolin-4 (1H)-one (3.1 g, 0.01 mol) and 50 ml of acetic acid were added to a 100 ml three-necked flask and stirred to be dissolved. Activated zinc powder (3.3 g, 0.05 mol) and 10 ml of methanol were then added; temperature was raised to 45° C. and mixture was stirred for 5 h. TLC tracking was performed until the completion of the reaction. The reaction was stopped and suction filtration was performed. The filter cake was washed with a large amount of ethyl acetate; solvent was removed under reduced pressure; and 50 ml water and 100 ml ethyl acetate were added to the residue. Organic layer was removed and the pH of aqueous layer was adjusted to 12 with 5M sodium hydroxide. A large amount of light yellow solid was precipitated and subjected to suction filtration and water washing. The filter cake was dried to give 1.7 g of a light yellow solid with a yield of 58.1%.

Step 9. Preparation of 4-Amino-5-cyano-6-((1-(8-chloro-4-oxo-2-phenyl-1,4-dihydroquinolin-3-yl) ethyl)amino)pyrimidine

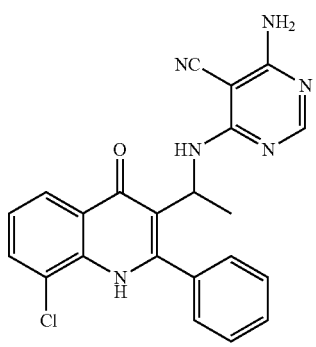 [SMILES: CC(Nc1ncnc(N)c1C#N)c1c(-c2ccccc2)[nH]c2c(Cl)cccc2c1=O]

3-(1-Aminoethyl)-8-chloro-2-phenylquinolin-4(1H)-one (1.5 g, 0.005 mol) and 50 ml of isopropanol were added to a 100 ml three-necked flask and stirred to be dissolved. 4-Amino-5-cyano-6-chloropyrimidine (0.93 g, 0.006 mol) and potassium carbonate (2.1 g, 0.015 mol) were then added; the temperature was raised to 80° C. and reaction was carried out under reflux for 5 h with stirring. TLC tracking was performed until the completion of the reaction for compound 9. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 1.3 g of a white solid was obtained with a yield of 62.2%.

$^1$H NMR (500 MHz, DMSO-d$_6$) δ: 11.06 (s, 1H), 8.23~8.21 (d, 1H, J=10.0 Hz), 8.01~7.99 (d, 1H, J=10.0 Hz), 7.90 (s, 1H), 7.88 (s, 1H), 7.59~7.52 (m, 5H), 7.40~7.43 (t, 1H, J=7.5 Hz), 7.24 (s, 2H), 5.14~5.17 (m, 1H), 1.39~1.37 (d, 3H, J=10.0 Hz). ES: m/z 416.9[M+H]$^+$.

Example 10. 4-Amino-5-cyano-6-((1-(4-oxo-2-phenyl-1,4-dihydroquinolin-3-yl) ethyl) amino) pyrimidine

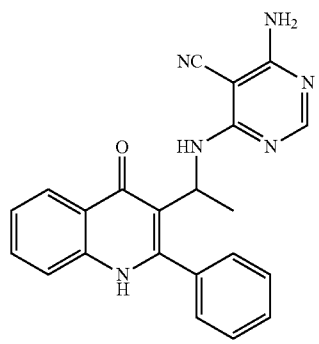 [SMILES: CC(Nc1ncnc(N)c1C#N)c1c(-c2ccccc2)[nH]c2ccccc2c1=O]

The preparation method was the same as the method of Example 9, except that 2-amino-3-chlorobenzoic acid in the materials was replaced with 2-aminobenzoic acid to generate a subject compound with a yield of 66.6%.

$^1$H NMR (500 MHz, DMSO-d$_6$) δ: 11.06 (s, 1H), 8.36~8.35 (d, 1H, J=5.0 Hz), 8.21~8.20 (d, 1H, J=5.0 Hz), 7.87 (s, 1H), 7.81~7.82 (m, 2H), 7.62~7.63 (m, 3H), 7.44~7.51 (m, 3H), 7.17 (s, 2H), 4.90~4.87 (m, 1H), 1.29~1.31 (d, 3H, J=10.0 Hz). ES: m/z 383.1[M+H]$^+$.

Example 11. 4-Amino-5-cyano-6-((1-(5-chloro-4-oxo-2-phenyl-1,4-dihydroquinolin-3-yl)ethyl)amino) pyrimidine

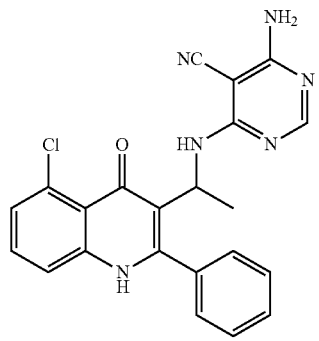 [SMILES: CC(Nc1ncnc(N)c1C#N)c1c(-c2ccccc2)[nH]c2cccc(Cl)c2c1=O]

The preparation method was the same as the method of Example 9, except that 2-amino-3-chlorobenzoic acid in the materials was replaced with 2-amino-6-chlorobenzoic acid to generate a subject compound with a yield of 58.6%.

$^1$H NMR (500 MHz, DMSO-d$_6$) δ: 11.05 (s, 1H), 8.24~8.22 (d, 1H, J=10.0 Hz), 8.02~8.00 (d, 1H, J=10.0 Hz), 7.91 (s, 1H), 7.86 (s, 1H), 7.55~7.51 (m, 5H), 7.41~7.44 (t, 1H, J=7.5 Hz), 7.24 (s, 2H), 5.14~5.17 (m, 1H), 1.38~1.36 (d, 3H, J=10.0 Hz). ES: m/z 416.9[M+H]$^+$.

Example 12. 4-Amino-5-cyano-6-((1-(8-fluoro-4-oxo-2-phenyl-1,4-dihydroquinolin-3-yl) ethyl) amino) pyrimidine

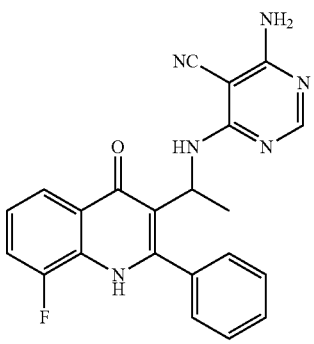 [SMILES: CC(Nc1ncnc(N)c1C#N)c1c(-c2ccccc2)[nH]c2c(F)cccc2c1=O]

The preparation method was the same as the method of Example 9, except that 2-amino-3-chlorobenzoic acid in the materials was replaced with 2-amino-3-fluorobenzoic acid to generate a subject compound with a yield of 62.1%.

$^1$H NMR (500 MHz, DMSO-d$_6$) δ: 11.06 (s, 1H), 8.22~8.20 (d, 1H, J=10.0 Hz), 8.02~8.00 (d, 1H, J=10.0 Hz), 7.91 (s, 1H), 7.88 (s, 1H), 7.59~7.53 (m, 5H), 7.40~7.43 (t, 1H, J=7.5 Hz), 7.24 (s, 2H), 5.14~5.16 (m, 1H), 1.39~1.37 (d, 3H, J=10.0 Hz). ES: m/z 400.9[M+H]$^+$.

Example 13. 4-Amino-5-cyano-6-((1-(4-oxo-2-phenyl-1,4-dihydroquinolin-3-yl) propyl)amino)pyrimidine

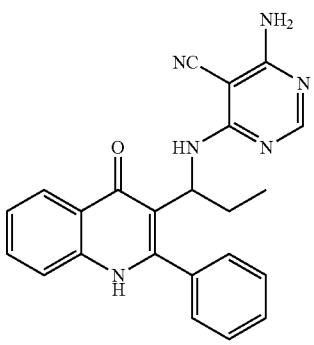 [SMILES: CCC(Nc1ncnc(N)c1C#N)c1c(-c2ccccc2)[nH]c2ccccc2c1=O]

The preparation method was the same as the method of Example 9, except that 2-amino-3-chlorobenzoic acid in the materials was replaced with 2-aminobenzoic acid and methylmagnesium chloride was replaced with ethylmagnesium chloride to generate a subject compound with a yield of 52.6%.

$^1$H NMR (500 MHz, DMSO-d$_6$) δ: 11.06 (s, 1H), 8.34~8.35 (d, 1H, J=5.0 Hz), 8.21~8.22 (d, 1H, J=5.0 Hz), 7.88 (s, 1H), 7.80~7.81 (m, 2H), 7.62~7.63 (m, 3H), 7.44~7.51 (m, 3H), 7.17 (s, 2H), 5.09~5.12 (m, 1H), 1.80~1.84 (m, 2H), 0.59~0.62 (m, 3H). ES: m/z 397.2[M+H]$^+$.

Example 14. 4-Amino-5-cyano-6-(((8-chloro-4-oxo-2-phenyl-1,4-dihydroquinolin-3-yl)methyl)amino) pyrimidine

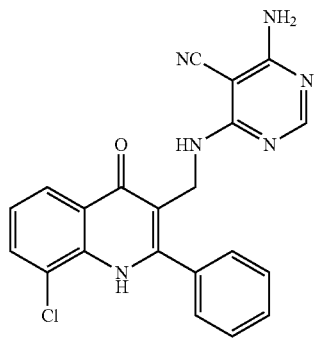 [SMILES: N#Cc1c(N)ncnc1NCc1c(-c2ccccc2)[nH]c2c(Cl)cccc2c1=O]

Step 1. Preparation of 8-Chloro-4-oxo-2-phenyl-1, 4-dihydroquinoline-3-formaldehyde oxime

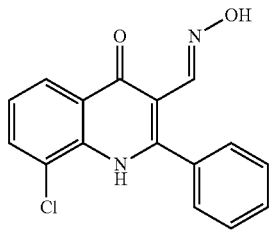 [SMILES: O=c1c(/C=N/O)c(-c2ccccc2)[nH]c2c(Cl)cccc12]

8-Chloro-4-oxo-2-phenyl-1,4-dihydroquinoline-3-carbaldehyde (4.3 g, 0.015 mol) obtained in steps 1~4 of Example 9 and 50 ml anhydrous methanol were added to a 100 ml three-necked flask and stirred to be dissolved. Hydroxylamine hydrochloride (6.3 g, 0.09 mol) and sodium acetate (9.8 g, 0.12 mol) were then added; temperature was raised to 45° C. and mixture was stirred for 5 h. TLC tracking was performed until the completion of the reaction. The reaction was stopped; solvent was removed under reduced pressure and 100 ml water was added to the residue. A large amount of light yellow solid was precipitated and subjected to suction filtration and water washing. The filter cake was dried to give 4.0 g of a light yellow solid with a yield of 88.9%.

Step 2. Preparation of 3-Aminomethyl-8-chloro-2-phenylquinolin-4(1H)-one

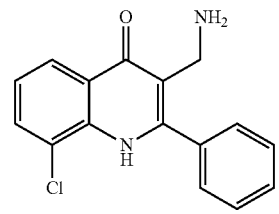 [SMILES: NCc1c(-c2ccccc2)[nH]c2c(Cl)cccc2c1=O]

8-Chloro-4-oxo-2-phenyl-1,4-dihydroquinoline-3-formaldehyde oxime (3.0 g, 0.01 mol) and 50 ml of acetic acid were added to a 100 ml three-necked flask and stirred to be dissolved. Activated zinc powder (3.3 g, 0.05 mol) and 10 ml of methanol were then added; temperature was raised to 45° C. and mixture was stirred for 5 h. TLC tracking was performed until the completion of the reaction. The reaction was stopped and suction filtration was performed. The filter cake was washed with a large amount of ethyl acetate; solvent was removed under reduced pressure; and 50 ml water and 100 ml ethyl acetate were added to the residue. Organic layer was removed and the pH of aqueous layer was adjusted to 12 with 5M sodium hydroxide. A large amount of light yellow solid was precipitated and subjected to suction filtration and water washing. The filter cake was dried to give 1.56 g of a light yellow solid with a yield of 55.2%.

Step 3. Preparation of 4-Amino-5-cyano-6-(((8-chloro-4-oxo-2-phenyl-1,4-dihydroquinolin-3-yl) methyl) amino) pyrimidine

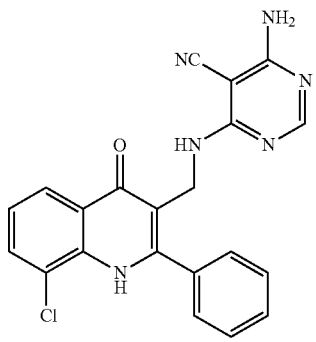 [SMILES: N#Cc1c(N)ncnc1NCc1c(-c2ccccc2)[nH]c2c(Cl)cccc2c1=O]

3-Aminomethyl-8-chloro-2-phenylquinolin-4(1H)-one (1.42 g, 0.005 mol) and 50 ml of isopropanol were added to a 100 ml three-necked flask and stirred to be dissolved. 4-Amino-5-cyano-6-chloropyrimidine (0.93 g, 0.006 mol) and potassium carbonate (2.1 g, 0.015 mol) were then added; the temperature was raised to 80° C. and reaction was carried out under reflux for 5 h with stirring. TLC tracking was performed until the completion of the reaction for compound 9. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 1.37 g of a white solid was obtained with a yield of 68.1%.

$^1$H NMR (500 MHz, DMSO-$d_6$) δ: 10.78 (s, 1H), 8.18~8.17 (d, 1H, J=5.0 Hz), 7.86~7.85 (d, 1H, J=5.0 Hz), 7.57~7.53 (m, 4H), 7.33~7.38 (t, 1H, J=7.5 Hz), 6.3 6~6.43 (m, 3H), 6.14 (s, 2H), 4.21 (s, 2H). ES: m/z 403.1[M+H]$^+$.

Example 15. 4-Amino-5-cyano-6-(((8-chloro-2-phenyl-1,4-dihydroquinolin-3-yl) methyl)amino) pyrimidine

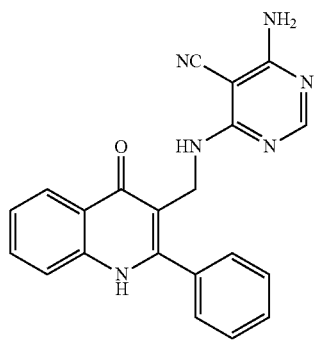 [SMILES: N#Cc1c(N)ncnc1NCc1c(-c2ccccc2)[nH]c2ccccc2c1=O]

Step 1. Preparation of 4-Oxo-2-phenyl-1,4-dihydroquinoline-3-carbaldehyde

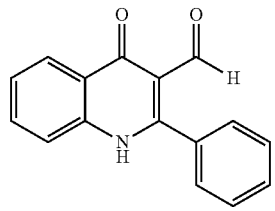 [SMILES: O=Cc1c(-c2ccccc2)[nH]c2ccccc2c1=O]

The preparation method was the same as the method for preparing 8-chloro-4-oxo-2-phenyl-1,4-dihydroquinoline-3-carbaldehyde in steps 1~4 of Example 9, except that 2-amino-3-chlorobenzoic acid in the materials was replaced with 2-aminobenzoic acid to generate a subject compound.

Step 2. Preparation of 3-Aminomethyl-2-phenylquinolin-4 (1H)-one

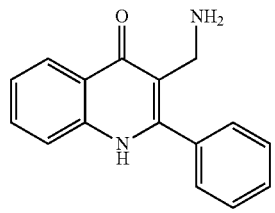 [SMILES: NCc1c(-c2ccccc2)[nH]c2ccccc2c1=O]

The preparation method was the same as the method for preparing 3-aminomethyl-8-chloro-2-phenylquinolin-4 (1H)-one in the steps 1~2 of Example 14, except that 8-chloro-4-oxo-2-phenyl-1,4-dihydroquinoline-3-carbaldehyde in the materials was replaced with 4-oxo-2-phenyl-1,4-dihydroquinoline-3-carbaldehyde obtained in the above step to generate a subject compound.

Step 3. Preparation of 4-Amino-5-cyano-6-(((8-chloro-2-phenyl-1,4-dihydroquinolin-3-yl) methyl) amino) pyrimidine

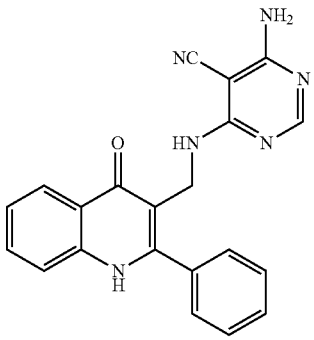 [SMILES: N#Cc1c(N)ncnc1NCc1c(-c2ccccc2)[nH]c2ccccc2c1=O]

3-Aminomethyl-2-phenylquinolin-4(1H)-one (1.25 g, 0.005 mol) and 50 ml of isopropanol were added to a 100 ml three-necked flask and stirred to be dissolved. 4-amino-5-cyano-6-chloropyrimidine (0.93 g, 0.006 mol) and potassium carbonate (2.1 g, 0.015 mol) were then added; the temperature was raised to 80° C. and reaction was carried out under reflux for 5 h with stirring. TLC tracking was performed until the completion of the reaction. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 1.37 g of a white solid was obtained with a yield of 68.1%.
$^1$H NMR (500 MHz, DMSO-d$_6$) δ: 10.80 (s, 1H), 8.18~8.17 (d, 1H, J=5.0 Hz), 7.88~7.87 (d, 1H, J=5.0 Hz), 7.56~7.54 (m, 5H), 7.36~7.39 (t, 1H, J=7.5 Hz), 6.43 (s, 3H), 6.10 (s, 2H), 4.23 (s, 2H). ES: m/z 368.9[M+H]$^+$.

Example 16. 4-Amino-5-cyano-6-(((8-fluoro-4-oxo-2-phenyl-1,4-dihydroquinolin-3-yl) methyl)amino) pyrimidine

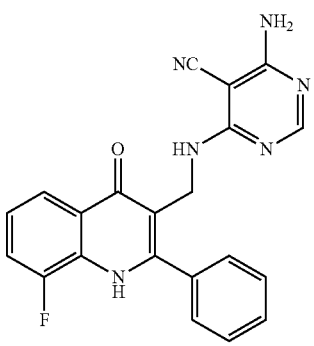

Step 1. Preparation of 3-Aminomethyl-8-fluoro-2-phenylquinolin-4(1H)-one

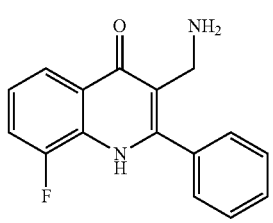 [SMILES: NCc1c(-c2ccccc2)[nH]c2c(F)cccc2c1=O]

The preparation method was the same as the method for preparing 3-aminomethyl-8-chloro-2-phenylquinolin-4(1H)-one in steps 1~2 of Example 14, except that 2-amino-3-chlorobenzoic acid in the materials was replaced with 2-amino-3-fluorobenzoic acid to generate a subject compound.

Step 2. Preparation of 4-Amino-5-cyano-6-(((8-fluoro-4-oxo-2-phenyl-1,4-dihydroquinolin-3-yl) methyl) amino)pyrimidine 3-Aminomethyl-8-fluoro-2-phenylquinolin-4(1H)-one (1.34 g, 0.005 mol) and 50 ml of isopropanol were added to a 100 ml three-necked flask and stirred to be dissolved. 4-Amino-5-cyano-6-chloropyrimidine (0.93 g, 0.006 mol) and potassium carbonate (2.1 g, 0.015 mol) were then added; the temperature was raised to 80° C. and reaction was carried out under reflux for 5 h with stirring. TLC tracking was performed until the completion of the reaction. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 1.23 g of a white solid was obtained with a yield of 63.8%.
$^1$H NMR (500 MHz, DMSO-d$_6$) δ: 10.78 (s, 1H), 8.18~8.17 (d, 1H, J=5.0 Hz), 7.86~7.85 (d, 1H, J=5.0 Hz), 7.57~7.53 (m, 4H), 7.33~7.38 (t, 1H, J=7.5 Hz), 6.36~6.43 (m, 3H), 6.14 (s, 2H), 4.21 (s, 2H). ES: m/z 387.1[M+H]$^+$.

Example 17. 2,4-Diamino-5-cyano-6-(((2-phenyl-1,4-dihydroquinolin-3-yl)methyl) amino) pyrimidine

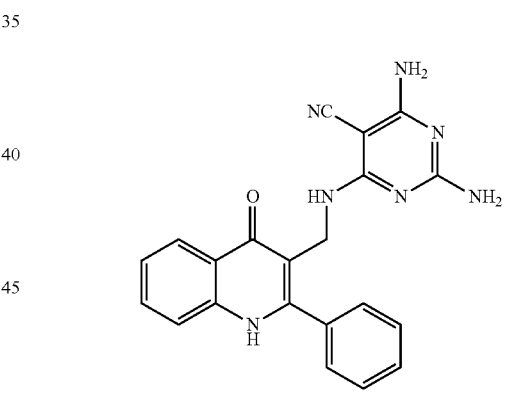

3-Aminomethyl-2-phenylquinolin-4(1H)-one (1.25 g, 0.005 mol) obtained in step 2 of Example 15 and 50 ml of isopropanol were added to a 100 ml three-necked flask and stirred to be dissolved. 2,4-diamino-5-cyano-6-chloropyrimidine (1.01 g, 0.006 mol) and DBU (2.1 g, 0.015 mol) were then added; the temperature was raised to 80° C. and reaction was carried out under reflux for 5 h with stirring. TLC tracking was performed until the completion of the reaction. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 0.70 g of a white solid was obtained with a yield of 36.3%.
$^1$H NMR (500 MHz, DMSO-d$_6$) δ: 10.81 (s, 1H), 8.18-8.17 (d, 1H, J=5.0 Hz), 7.89-7.88 (d, 1H, J=5.0 Hz), 7.56-

7.54 (m, 4H), 7.36-7.39 (t, 1H, J=7.5 Hz), 6.43 (s, 3H), 6.10 (s, 2H), 6.02 (s, 2H), 4.23 (s, 2H). ES: m/z 384.1[M+H]⁺.

Example 18. 2,4-Diamino-5-cyano-6-((8-chloro-4-oxo-2-phenyl-1,4-dihydroquinolin-3-yl)methyl)amino)pyrimidine

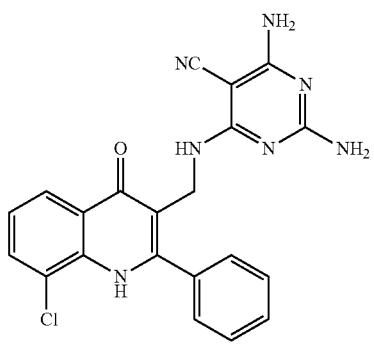 [SMILES: N#Cc1c(N)nc(N)nc1NCc1c(-c2ccccc2)[nH]c2c(Cl)cccc2c1=O]

3-Aminomethyl-8-chloro-2-phenylquinolin-4(1H)-one (1.42 g, 0.005 mol) obtained in step 2 of Example 14 and 50 ml of isopropanol were added to a 100 ml three-necked flask and stirred to be dissolved. 2,4-diamino-5-cyano-6-chloropyrimidine (1.01 g, 0.006 mol) and potassium carbonate (2.1 g, 0.015 mol) were then added; the temperature was raised to 80° C. and reaction was carried out under reflux for 5 h with stirring. TLC tracking was performed until the completion of the reaction. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 0.62 g of a white solid was obtained with a yield of 29.6%.

¹H NMR (500 MHz, DMSO-d₆) δ: 10.78 (s, 1H), 8.17~8.18 (d, 1H, J=5.0 Hz), 7.85~7.86 (d, 1H, J=5.0 Hz), 7.51~7.54 (m, 3H), 7.33~7.38 (t, 1H, J=7.5 Hz), 6.36~6.43 (m, 3H), 6.16 (s, 2H), 6.08 (s, 2H), 4.21 (s, 2H). ES: m/z 418.1[M+H]⁺.

Example 19. 4-Amino-5-cyano-6-((1-(8-chloro-1-methyl-4-oxo-2-phenyl-1,4-dihydroquinolin-3-yl)ethyl)amino)pyrimidine

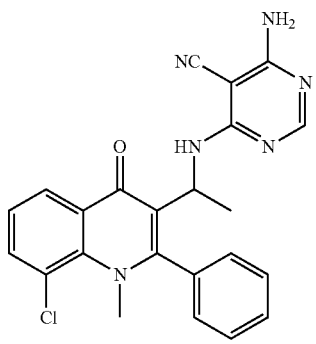 [SMILES: CC(Nc1ncnc(N)c1C#N)c1c(-c2ccccc2)n(C)c2c(Cl)cccc2c1=O]

Step 1. Preparation of tert-butyl (1-(8-Chloro-4-oxo-2-phenyl-1,4-dihydroquinolin-3-yl)ethyl) carbamate

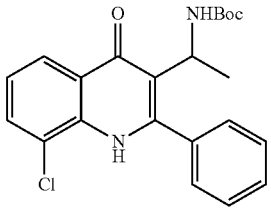 [SMILES: CC(NC(=O)OC(C)(C)C)c1c(-c2ccccc2)[nH]c2c(Cl)cccc2c1=O]

3-(1-Aminoethyl)-8-chloro-2-phenylquinolin-4(1H)-one (1.5 g, 0.005 mol) obtained in step 8 of Example 9 and 20 ml of THF were added to a 100 ml three-necked flask and stirred to be dissolved. 10 ml 1M sodium hydroxide solution was added and the temperature was reduced to 0° C. A solution of di-tert-butyl dicarbonate (1.38 g, 0.006 mol) in 5 ml of tetrahydrofuran was added dropwise and the mixture was stirred at room temperature for 1 h. TLC tracking was performed until the completion of the reaction. The reaction was stopped and tetrahydrofuran was removed by spin evaporation. 50 ml of water and 50 ml of ethyl acetate were added to the residue, and the aqueous layer was extracted with 25 ml×2 ethyl acetate. The organic layers were combined, washed with saturated salt water, dried over anhydrous sodium sulfate, and solvent was distilled off under reduced pressure. Column chromatography was performed to give 1.65 g of a white solid with a yield of 82.8%.

Step 2. Preparation of tert-butyl (1-(8-Chloro-1-methyl-4-oxo-2-phenyl-1,4-dihydroquinolin-3-yl)ethyl)carbamate

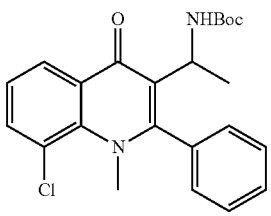 [SMILES: CC(NC(=O)OC(C)(C)C)c1c(-c2ccccc2)n(C)c2c(Cl)cccc2c1=O]

tert-butyl (1-(8-Chloro-4-oxo-2-phenyl-1,4-dihydroquinolin-3-yl)ethyl)carbamate (1.59 g, 0.004 mol), potassium carbonate (1.69 g, 0.012 mol), methyl iodide (2.84 g, 0.020 mol) and 25 ml DMF were added to a 100 ml three-necked flask. The temperature was raised to 45° C. and the mixture was stirred for 2 h. TLC tracking was performed until the completion of the reaction. The reaction was stopped and suction filtration was performed. The filter cake was washed with a large amount of ethyl acetate and solvent was removed under reduced pressure. 50 ml of water and 50 ml of ethyl acetate were added for extraction, and the aqueous layer was washed with 25 ml×2 ethyl acetate. The organic layers were combined, washed with saturated sodium chloride aqueous solution. After drying, the solvent was removed to give 1.53 g of a white solid with a yield of 92.6%.

Step 3. Preparation of 3-(1-Aminoethyl)-8-chloro-1-methyl-2-phenylquinolin-4 (1H)-one hydrochloride

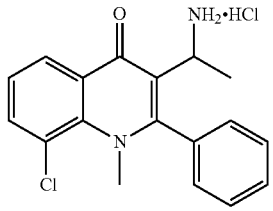

tert-butyl (1-(8-Chloro-1-methyl-4-oxo-2-phenyl-1,4-dihydroquinolin-3-yl)ethyl) carbamate (1.24 g, 0.003 mol) and 20 ml of hydrogen chloride in ethanol (HCl concentration of 6.2M) were added to a 100 ml three-necked flask and stirred at room temperature for 1 h. TLC tracking was performed until the completion of the reaction. The reaction was stopped and solvent was removed by spin evaporation. 50 ml anhydrous ethanol was added and solvent was removed again by spin evaporation to generate 1.21 g crude product which was used directly in the next step.

Step 4. Preparation of 4-Amino-5-cyano-6-((1-(8-chloro-1-methyl-4-oxo-2-phenyl-1,4-dihydroquinolin-3-yl) ethyl) amino) pyrimidine

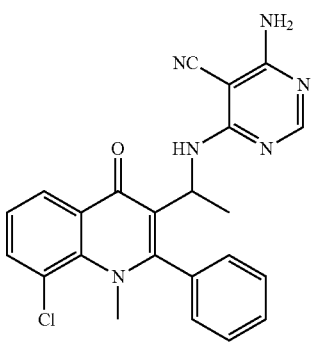 [SMILES: CC(Nc1ncnc(N)c1C#N)c1c(-c2ccccc2)n(C)c2c(Cl)cccc2c1=O]

Crude 3-(1-aminoethyl)-8-chloro-1-methyl-2-phenylquinolin-4(1H)-one hydrochloride (1.21 g) and 50 ml of isopropanol were added to a 100 ml three-necked flask and stirred to be dissolved. 4-Amino-5-cyano-6-chloropyrimidine (0.36 g, 0.036 mol) and potassium carbonate (1.25 g, 0.09 mol) were then added; the temperature was raised to 80° C. and reaction was carried out under reflux for 5 h with stirring. TLC tracking was performed until the completion of the reaction for compound 9. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 0.93 g of a white solid was obtained with a yield of 72.1%.

$^1$H NMR (500 MHz, DMSO-$d_6$) δ: 8.36~8.35 (d, 1H, J=5.0 Hz), 8.21~8.20 (d, 1H, J=5.0 Hz), 7.87 (s, 1H), 7.81~7.82 (m, 2H), 7.62~7.63 (m, 2H), 7.44~7.51 (m, 3H), 7.17 (s, 2H), 4.90~4.87 (m, 1H), 3.42 (s, 3H), 1.29~1.31 (d, 3H, J=10.0 Hz). ES: m/z 430.9[M+H]$^+$.

Example 20. 4-Amino-5-cyano-6-((1-(8-fluoro-1-methyl-4-oxo-2-phenyl-1,4-dihydroquinolin-3-yl)ethyl)amino)pyrimidine

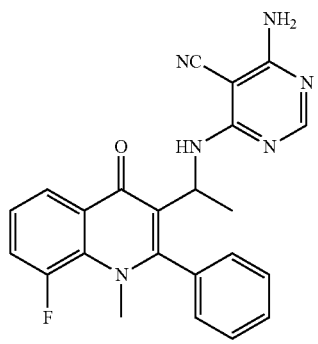 [SMILES: CC(Nc1ncnc(N)c1C#N)c1c(-c2ccccc2)n(C)c2c(F)cccc2c1=O]

Step 1. Preparation of 3-(1-Aminoethyl)-8-fluoro-2-phenylquinolin-4(1H)-one

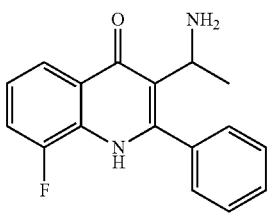 [SMILES: CC(N)c1c(-c2ccccc2)[nH]c2c(F)cccc2c1=O]

The preparation method was the same as the method for preparing 3-(1-aminoethyl)-8-chloro-2-phenylquinolin-4 (1H)-one in the steps 1~8 of Example 9, except that 2-amino-3-chlorobenzoic acid in the materials was replaced with 2-amino-3-fluorobenzoic acid to generate a subject compound.

Step 2. Preparation of 3-(1-Aminoethyl)-8-fluoro-1-methyl-2-phenylquinolin-4(1H)-one hydrochloride

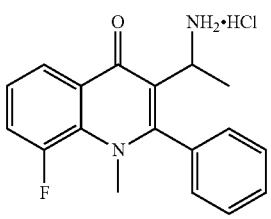

The preparation method was the same as the method for preparing 3-(1-aminoethyl)-8-chloro-1-methyl-2-phenylquinolin-4 (1H)-one hydrochloride in the steps 1~3 of Example 19, except that 3-(1-aminoethyl)-8-chloro-2-phenylquinolin-4(1H)-one in the materials was replaced with 3-(1-aminoethyl)-8-fluoro-2-phenylquinolin-4(1H)-one obtained in the above step to generate a subject compound.

Step 3. Preparation of 4-Amino-5-cyano-6-((1-(8-fluoro-1-methyl-4-oxo-2-phenyl-1,4-dihydroquinolin-3-yl)ethyl)amino)pyrimidine Crude 3-(1-aminoethyl)-8-fluoro-1-methyl-2-phenylquinolin-4(1H)-one hydrochloride (1.18 g) and 50 ml of isopropanol were added to a 100 ml three-necked flask and stirred to be dissolved. 4-Amino-5-cyano-6-chloropyrimidine (0.36 g, 0.036 mol) and potassium carbonate (1.25 g, 0.09 mol) were then added; the temperature was raised to 80° C. and reaction was carried out under reflux for 5 h with stirring. TLC tracking was performed until the completion of the reaction for compound 9. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 0.93 g of a white solid was obtained with a yield of 72.1%.

$^1$H NMR (500 MHz, DMSO-$d_6$) δ: 8.38~8.37 (d, 1H, J=5.0 Hz), 8.20~8.19 (d, 1H, J=5.0 Hz), 7.87 (s, 1H), 7.81~7.83 (m, 2H), 7.61~7.63 (m, 2H), 7.44~7.50 (m, 3H), 7.16 (s, 2H), 4.90~4.86 (m, 1H), 3.41 (s, 3H), 1.29~1.31 (d, 3H, J=10.0 Hz). ES: m/z 415.2[M+H]$^+$.

Example 21. 4-Amino-5-cyano-6-((1-(1-methyl-4-oxo-2-phenyl-1,4-dihydroquinolin-3-yl) methyl) amino) pyrimidine

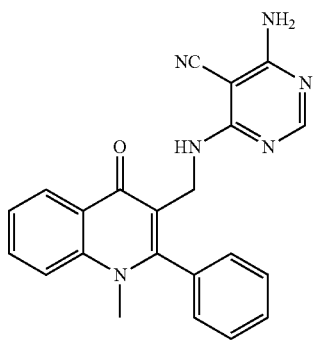 [SMILES: Cn1c(-c2ccccc2)c(CNc2ncnc(N)c2C#N)c(=O)c2ccccc21]

Step 1. Preparation of 3-(1-Aminoethyl)-1-methyl-2-phenylquinolin-4(1H)-one hydrochloride

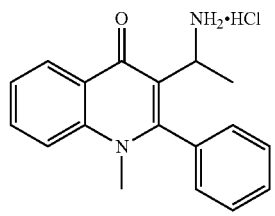

The preparation method was the same as the method for preparing 3-(1-aminoethyl)-8-chloro-1-methyl-2-phenylquinolin-4(1H)-one hydrochloride in the steps 1~3 of Example 19, except that 3-(1-aminoethyl)-8-chloro-2-phenylquinolin-4(1H)-one in the materials was replaced with 3-aminomethyl-2-phenylquinolin-4(1H)-one obtained in step 2 of Example 15 to generate a subject compound.

Step 2. Preparation of 4-Amino-5-cyano-6-((1-(1-methyl-4-oxo-2-phenyl-1,4-dihydroquinolin-3-yl) methyl)amino)pyrimidine Crude 3-(1-aminoethyl)-1-methyl-2-phenylquinolin-4(1H)-one hydrochloride (1.12 g) and 50 ml of isopropanol were added to a 100 ml three-necked flask and stirred to be dissolved. 4-Amino-5-cyano-6-chloropyrimidine (0.36 g, 0.036 mol) and potassium carbonate (1.25 g, 0.09 mol) were then added; the temperature was raised to 80° C. and reaction was carried out under reflux for 5 h with stirring. TLC tracking was performed until the completion of the reaction. The reaction was stopped and suction filtration was performed. The filter cake was washed with a large amount of ethyl acetate; solvent was removed under reduced pressure; and methanol and silica gel were added to the residue for preparing a mixture for chromatography. After column chromatography separation, 0.79 g of a white solid was obtained with a yield of 68.5%.

$^1$H NMR (500 MHz, DMSO-$d_6$) δ: 8.17~8.18 (d, 1H, J=5.0 Hz), 7.86~7.87 (d, 1H, J=5.0 Hz), 7.48~7.53 (m, 5H), 7.36~7.39 (t, 1H, J=7.5 Hz), 6.43 (s, 3H), 6.10 (s, 2H), 4.23 (s, 2H), 3.41 (s, 3H). ES: m/z 383.2[M+H]$^+$.

Example 22. 2,4-Diamino-5-cyano-6-((1-(4-oxo-2-phenyl-1,4-dihydroquinolin-3-yl) ethyl)amino)pyrimidine

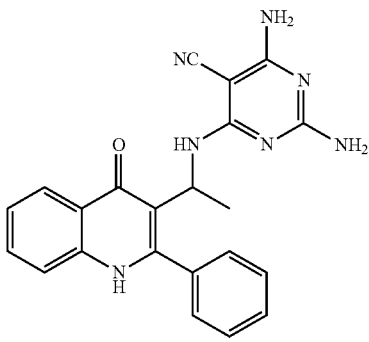

The preparation method was the same as the method of Example 9, except that 2-amino-3-chlorobenzoic acid in the materials was replaced with 2-aminobenzoic acid, and 4-amino-5-cyano-6-chloropyrimidine in the materials was replaced with 2,4-diamino-5-cyano-6-chloropyrimidine to generate a subject compound with a yield of 45.1%.

$^1$H NMR (500 MHz, DMSO-$d_6$) δ: 11.05 (s, 1H), 8.35~8.34 (d, 1H, J=5.0 Hz), 8.22~8.21 (d, 1H, J=5.0 Hz), 7.81~7.82 (m, 2H), 7.61~7.62 (m, 3H), 7.45~7.52 (m, 3H), 6.11 (s, 2H), 6.03 (s, 2H), 4.90~4.87 (m, 1H), 1.29~1.31 (d, 3H, J=10.0 Hz). ES: m/z 398.2[M+H]$^+$.

Example 23. 2,4-Diamino-5-cyano-6-((1-(8-chloro-4-oxo-2-phenyl-1,4-dihydroquinolin-3-yl)ethyl)amino)pyrimidine

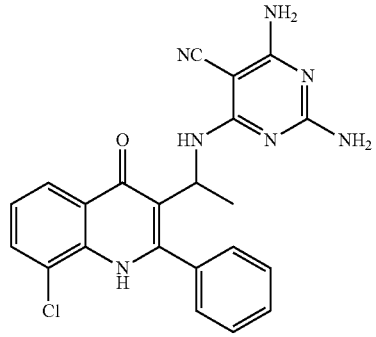 [SMILES: CC(Nc1nc(N)nc(N)c1C#N)c1c(-c2ccccc2)[nH]c2c(Cl)cccc2c1=O]

The preparation method was the same as the method of Example 9, except that 4-amino-5-cyano-6-chloropyrimidine in the materials was replaced with 2,4-diamino-5-cyano-6-chloropyrimidine to generate a subject compound with a yield of 32.1%.

$^1$H NMR (500 MHz, DMSO-d$_6$) δ: 11.05 (s, 1H), 8.20~8.22 (d, 1H, J=10.0 Hz), 8.00~8.02 (d, 1H, J=10.0 Hz), 7.91 (s, 1H), 7.53~7.58 (m, 5H), 7.40~7.43 (t, 1H, J=7.5 Hz), 6.12 (s, 2H), 6.04 (s, 2H), 5.14~5.17 (m, 1H), 1.35~1.37 (d, 3H, J=10.0 Hz). ES: m/z 432.1 [M+H]$^+$.

Example 24. 4-Amino-5-cyano-6-((1-(1-methyl-4-oxo-2-phenyl-1,4-dihydroquinolin-3-yl) ethyl) amino) pyrimidine

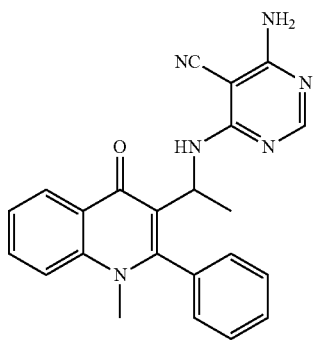 [SMILES: CC(Nc1ncnc(N)c1C#N)c1c(-c2ccccc2)n(C)c2ccccc2c1=O]

The preparation method was the same as the method of Example 20, except that 2-amino-3-fluorobenzoic acid in the materials was replaced with 2-aminobenzoic acid to generate a subject compound with a yield of 81.1%.

$^1$H NMR (500 MHz, DMSO-d$_6$) δ: 8.36-8.35 (d, 1H, J=5.0 Hz), 8.21-8.20 (d, 1H, J=5.0 Hz), 7.87 (s, 1H), 7.81-7.82 (m, 2H), 7.62-7.63 (m, 2H), 7.44-7.51 (m, 4H), 7.17 (s, 2H), 4.90-4.87 (m, 1H), 3.42 (s, 3H), 1.29-1.31 (d, 3H, J=10.0 Hz). ES: m/z 397.2[M+H]$^+$.

Example 25. 2,4-Diamino-5-cyano-6-((1-(1-methyl-4-oxo-2-phenyl-1,4-dihydroquinolin-3-yl) ethyl) amino) pyrimidine

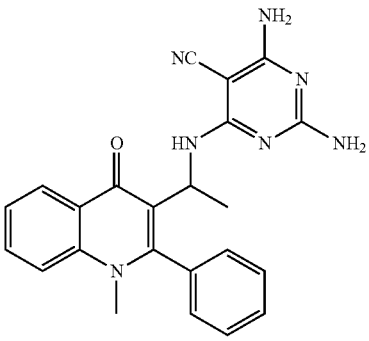 [SMILES: CC(Nc1nc(N)nc(N)c1C#N)c1c(-c2ccccc2)n(C)c2ccccc2c1=O]

The preparation method was the same as the method of Example 20, except that 2-amino-3-fluorobenzoic acid in the materials was replaced with 2-aminobenzoic acid, and 4-amino-5-cyano-6-chloropyrimidine in the materials was replaced with 2,4-diamino-5-cyano-6-chloropyrimidine to generate a subject compound with a yield of 81.1%.

$^1$H NMR (500 MHz, DMSO-d$_6$) δ: 8.36-8.35 (d, 1H, J=5.0 Hz), 8.22-8.21 (d, 1H, J=5.0 Hz), 7.81-7.83 (m, 2H), 7.62-7.64 (m, 2H), 7.44-7.50 (m, 4H), 6.12 (s, 2H), 6.04 (s, 2H), 4.87-4.90 (m, 1H), 3.42 (s, 3H), 1.29-1.31 (d, 3H, J=10.0 Hz). ES: m/z 412.2[M+H]$^+$.

Example 26. 4-Amino-5-cyano-6-((1-(1-methyl-4-oxo-2-(3-fluorophenyl)-1,4-dihydroquinolin-3-yl) ethyl) amino) pyrimidine

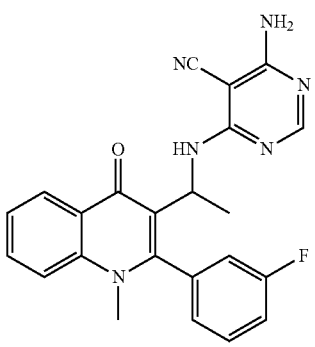 [SMILES: CC(Nc1ncnc(N)c1C#N)c1c(-c2cccc(F)c2)n(C)c2ccccc2c1=O]

The preparation method was the same as the method of Example 20, except that 2-amino-3-fluorobenzoic acid in the materials was replaced with 2-aminobenzoic acid and benzoyl ethyl ester in the materials was replaced with 3-fluorobenzoyl ethyl ester to generate a subject compound with a yield of 32.8%.

$^1$H NMR (500 MHz, DMSO-d$_6$) δ: 8.33-8.32 (d, 1H, J=5.0 Hz), 8.18-8.19 (d, 1H, J=5.0 Hz), 7.87 (s, 1H), 7.83-7.84 (m, 3H), 7.55-7.58 (m, 1H), 7.49-7.53 (m, 3H), 7.19 (s, 2H), 4.88-4.91 (m, 1H), 3.43 (s, 3H), 1.31-1.33 (d, 3H, J=10.0 Hz). ES: m/z 415.2[M+H]$^+$.

Example 27. 2,4-Diamino-5-cyano-6-((1-(8-chloro-1-methyl-4-oxo-2-phenyl-1,4-dihydroquinolin-3-yl)ethyl)amino)pyrimidine

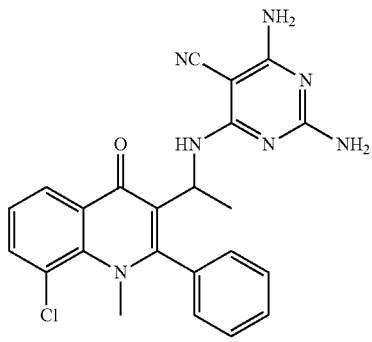 [SMILES: CC(Nc1nc(N)nc(N)c1C#N)c1c(-c2ccccc2)n(C)c2c(Cl)cccc2c1=O]

The preparation method was the same as the method of Example 20, except that 2-amino-3-fluorobenzoic acid in the materials was replaced with 2-amino-3-chlorobenzoic acid, and 4-amino-5-cyano-6-chloropyrimidine in the materials was replaced with 2,4-diamino-5-cyano-6-chloropyrimidine to generate a subject compound with a yield of 33.5%.

$^1$H NMR (500 MHz, DMSO-$d_6$) δ: 8.21~8.23 (d, 1H, J=10.0 Hz), 8.00~8.03 (d, 1H, J=10.0 Hz), 7.92 (s, 1H), 7.53~7.55 (m, 5H), 7.40~7.43 (t, 1H, J=7.5 Hz), 6.15 (s, 2H), 6.01 (s, 2H), 5.14~5.17 (m, 1H), 3.43 (s, 3H), 1.35~1.37 (d, 3H, J=10.0 Hz). ES: m/z 446.1[M+H]$^+$.

Example 28. 2,4-Diamino-5-cyano-6-((8-fluoro-4-oxo-2-phenyl-1,4-dihydroquinolin-3-yl) methyl)amino)pyrimidine

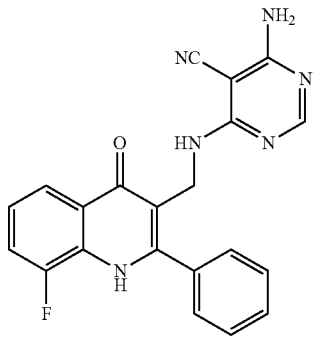

The preparation method was the same as the method of Example 15, except that 2-aminobenzoic acid in the materials was replaced with 2-amino-3-fluorobenzoic acid to generate a subject compound with a yield of 22.8%.

$^1$H NMR (500 MHz, DMSO-$d_6$) δ: 10.78 (s, 1H), 8.17~8.18 (d, 1H, J=5.0 Hz), 7.86~7.87 (d, 1H, J=5.0 Hz), 7.52~7.55 (m, 3H), 7.35~7.39 (t, 1H, J=7.5 Hz), 6.36~6.43 (m, 2H), 6.16 (s, 2H), 6.08 (s, 2H), 4.21 (s, 2H). ES: m/z 387.1[M+H]$^+$.

Example 29. Preparation of 4-Amino-5-cyano-6-(((5-chloro-4-oxo-2-phenyl-1,4-dihydroquinolin-3-yl) methyl)amino)pyrimidine

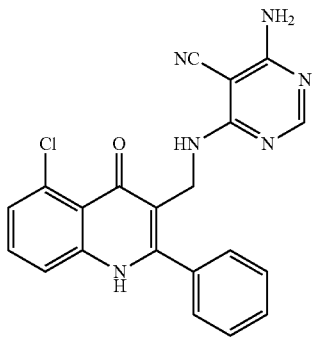 [SMILES: N#Cc1c(N)ncnc1NCc1c(-c2ccccc2)[nH]c2cccc(Cl)c2c1=O]

The preparation method was the same as the method of Example 15, except that 2-aminobenzoic acid in the materials was replaced with 2-amino-6-chlorobenzoic acid to generate a subject compound with a yield of 88.1%.

$^1$H NMR (500 MHz, DMSO-$d_6$) δ: 10.78 (s, 1H), 8.18~8.17 (d, 1H, J=5.0 Hz), 7.82~7.85 (d, 1H, J=5.0 Hz), 7.52~7.56 (m, 4H), 7.33~7.38 (t, 1H, J=7.5 Hz), 6.36~6.41 (m, 3H), 6.11 (s, 2H), 4.20 (s, 2H). ES: m/z 403.1[M+H]$^+$.

Example 30. 2,4-Diamino-5-cyano-6-(1-(2-(3-fluorophenyl)-4-oxo-4H-chromen-3-yl) ethylamino)pyrimidine

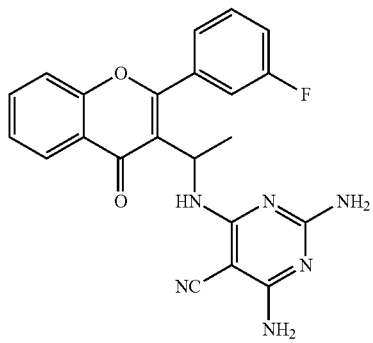 [SMILES: CC(Nc1nc(N)nc(N)c1C#N)c1c(-c2cccc(F)c2)oc2ccccc2c1=O]

Step 1. Preparation of 3-Bromomethyl-2-(3-fluorophenyl)-4H-chromen-4-one

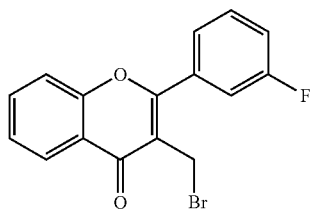 [SMILES: O=c1c(CBr)c(-c2cccc(F)c2)oc2ccccc12]

The preparation method was the same as the method for preparing 3-bromomethyl-2-phenyl-4H-chromen-4-one in steps 1~3 of Example 1, except that benzoyl chloride in the materials was replaced with 3-fluorobenzoyl chloride to generate a subject compound.

Step 2. Preparation of 2,4-Diamino-5-cyano-6-(1-(2-(3-fluorophenyl)-4-oxo-4H-chromen-3-yl) ethylamino) pyrimidine The preparation method was the same as the method of Example 3, except that 3-bromomethyl-2-phenyl-4H-chromen-4-one was replaced with 3-bromomethyl-2-(3-fluorophenyl)-4H-chromen-4-one obtained in the above step, and 4-amino-5-cyano-6-chloropyrimidine was replaced with 2,4-diamino-5-cyano-6-chloropyrimidine to generate a subject compound with a yield of 3.1%.
$^1$H NMR (300 MHz, DMSO-$d_6$) δ: 8.17-8.14 (d, 1H, J=7.8 Hz), 7.88-7.83 (t, 1H, J=7.5 Hz), 7.72-7.46 (m, 6H), 6.87-6.84 (d, 1H, J=9.0 Hz), 6.50 (s, 2H), 6.07 (br, 2H), 5.37-5.30 (t, 1H, J=6.9 Hz), 1.44-1.42 (d, 3H, J=6.6 Hz). ES: m/z 417.1[M+H]$^+$.

Example 31. 2,4-Diamino-5-cyano-6-(1-(2-(3,5-difluorophenyl)-4-oxo-4H-chromen-3-yl)ethylamino)pyrimidine

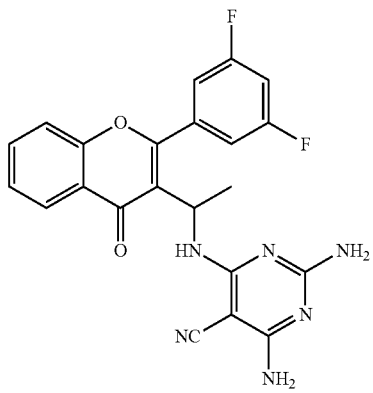 [SMILES: CC(Nc1nc(N)nc(N)c1C#N)c1c(-c2cc(F)cc(F)c2)oc2ccccc2c1=O]

The preparation method was the same as the method of Example 30, except that 3-fluorobenzoyl chloride in the materials was replaced with 3,5-difluorobenzoyl chloride acid to generate a subject compound with a yield of 7.9%.
$^1$H NMR (300 MHz, DMSO-$d_6$) δ: 8.17-8.14 (d, 1H, J=7.9 Hz), 7.89-7.83 (t, 1H, J=7.7 Hz), 7.68-7.65 (d, 1H, J=8.5 Hz), 7.58-7.52 (m, 4H), 6.81-6.78 (d, 1H, J=8.8 Hz), 6.60 (s, 2H), 6.08 (br, 2H), 5.37-5.27 (m, 1H), 1.45-1.43 (d, 3H, J=6.7 Hz). ES: m/z 435.1[M+H]$^+$.

Example 32. 2,4-Diamino-5-cyano-6-(1-(4-oxo-2-phenyl-4H-chromen-3-yl) propylamino) pyrimidine

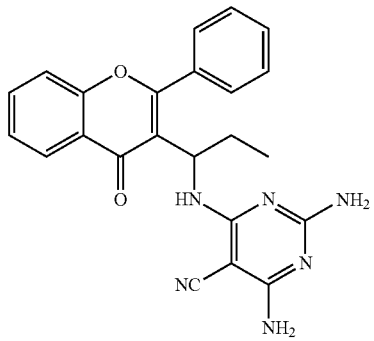 [SMILES: CCC(Nc1nc(N)nc(N)c1C#N)c1c(-c2ccccc2)oc2ccccc2c1=O]

The preparation method was the same as the method of Example 30, except that 3-fluorobenzoyl chloride in the materials was replaced with benzoyl chloride, and methylmagnesium chloride in the materials was replaced with ethylmagnesium chloride to generate a subject compound with a yield of 5.7%.
$^1$H NMR (300 MHz, DMSO-$d_6$) δ: 8.17~8.14 (d, 1H, J=7.8 Hz), 7.89~7.86 (t, 1H, J=7.7 Hz), 7.77~7.53 (m, 7H), 7.09~7.04 (s, 1H), 6.77 (s, 2H), 6.21 (br, 2H), 5.31~5.23 (m, 1H), 1.85~1.83 (m, 2H), 0.67~0.62 (t, 3H, J=7.0 Hz). ES: m/z 413.1[M+H]$^+$.

Comparative Example 1. 4-Amino-5-cyano-6-(1-(3-(3,5-difluorophenyl)-6-fluoro-1-methyl-4-oxo-1,4-dihydroquinoline-2-yl)ethylamino)pyrimidine

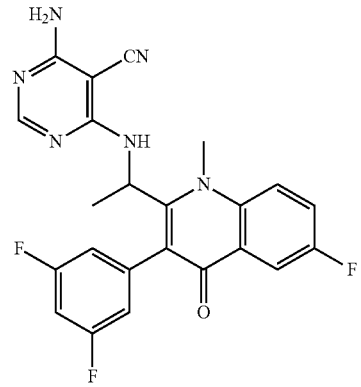 [SMILES: CC(Nc1ncnc(N)c1C#N)c1c(-c2cc(F)cc(F)c2)c(=O)c2cc(F)ccc2n1C]

The compound was prepared according to the method disclosed in Example 17 of WO2010/151735 and identified by 1H NMR spectrum and mass spectrometry. The in vitro kinase activity of the compound was determined by the method of the following Experiment 1, and the results showed that the IC$_{50}$ value of the compound against PI3Kδ was 20 nM and the selectivity was poor.

Experiment 1. Evaluation of In Vitro Kinase Activity of Compounds

1. Materials
Compounds: the compounds prepared in above examples of the present invention, each of which was prepared to a concentration of 10 mM in DMSO and diluted to 11 M, 100 nM, 10 nM, 1 nM, 0.1 nM, 0.01 nM successively.
Reagents: PI3Kα (p110α(p85a), purchased from Invitrogen, Cat.No. PV4788; PIK3Cδ (p110δ/p85a), purchased from Millipore, Cat.No. 14-604-K; PIK3Cβ (p110β), purchased from Millipore, Cat.No. 14-603-K; PIK3Cγ (pp110γ), purchased from Invitrogen, Cat.No. PR8641C; DMSO, purchased from Sigma; EDTA, purchased from Sigma; 1× kinase buffer (50 mM HEPES, pH 7.5, 0.0015% Brij-35, 10 mM MgCl$_2$, 2 mM DTT), which was prepared before use; termination solution (100 mM HEPES, pH 7.5, 0.015% Brij-35, 0.2% Coating Reagent#3, 50 mM EDTA), which was prepared before use.
Instruments: LabChip EZ Reader purchased from Caliper, USA.
2. Methods
2.1 10 μl solution of each concentration of each compound was placed into 96-well plate and 90 μl of 1× kinase buffer was added. DMSO control group and control group without kinase activity were set up, which all contained 10 μl DMSO and 90 μl of 1× kinase buffer. Each group was mixed well at room temperature for 10 min, and then 5 μl of each group was transferred to a 384-well plate.

2.2 Kinases were dissolved in 1× kinase buffer to prepare a 2.5× kinase solution. 10 μl of 2.5× kinase solution was transferred to the 384-well plate containing compounds of different concentrations. 10 μl of 2.5× kinase solution was added to DMSO control group and 10 μl of 1× kinase buffer without kinase was added to control group without kinase activity. The plate was incubated at room temperature for 10 min.

2.3 ATP and the polypeptide labeled with FAM were dissolved in 1× kinase buffer to prepare 2.5× substrate solution. Then 10 μl of 2.5× substrate solution was transferred to the 384-well plate and incubated at 28° C. for 1 h.

2.4 25 μl of termination solution was added to each well to terminate the reaction.

2.5 The plate was placed on the LabChip EZ Reader to read the data of conversion rate and inhibitory rate (I%) was calculated according to formula: I %=(Max−Com)/(Max−Min)×100, wherein Max was the conversion rate of DMSO control group, Min was the conversion rate of control group without kinase activity, Com was the conversion rate of compound treatment group. $IC_{50}$ was fitted by XLfit processing of the data. $IC_{50}$ represents the concentration of compound when the compound inhibits 50% of kinase activity compared with the group without compound. Some $IC_{50}$ results were shown in Table 1.

TABLE 1

| Kinase subtype Test compound | $IC_{50}$ (nM) | | | |
| --- | --- | --- | --- | --- |
| | PI3Kδ | PI3Kα | PI3Kβ | PI3Kγ |
| Example 2 | 13.5 | — | — | — |
| Example 3 | 17 | >1000 | >1000 | >1000 |
| Example 4 | 9.2 | >1000 | 546 | 83 |
| Example 5 | 11 | >1000 | >1000 | >1000 |
| Example 6 | 9.5 | >1000 | 881 | 84 |
| Example 7 | 5 | >1000 | >1000 | >1000 |
| Example 8 | 6.6 | >1000 | 385 | 134 |
| Example 9 | 3.8 | 219 | 139 | 66 |
| Example 10 | 4.4 | 1072 | 569 | 441 |
| Example 13 | 5.8 | >1000 | >1000 | >1000 |
| Example 14 | 3.2 | >1000 | 546 | 905 |
| Example 15 | 21 | >1000 | >1000 | >1000 |
| Example 18 | 2 | 336 | 99 | 61 |
| Example 22 | 11 | 675 | 635 | 60 |
| Example 23 | 1.4 | 114 | 60 | 5.7 |
| Example 25 | 1.8 | 127 | 113 | 21 |
| Example 26 | 2.3 | >1000 | 972 | 814 |
| Example 27 | 1.4 | 39 | 38 | 11 |
| Example 30 | 3.6 | >1000 | >1000 | 155 |
| Example 32 | 4.8 | >1000 | >1000 | 673 |

"—" means no detection.

The above experiment results showed that the compounds of the present invention have a good inhibitory activity against PI3K δ while a low inhibitory effect on PI3K α, PIK3 β and PIK3 γ. The compounds of the present invention have a high selectivity and are highly desirable as therapeutic agents which have a higher efficacy and a smaller side-effect for cancers, tissue proliferative diseases, or inflammatory diseases.

Experiment 2. Evaluation of In Vitro Cell Activity of Compounds

1. Materials

Compounds: the compounds prepared in above examples of the present invention, each of which was prepared to a concentration of 10 mM in DMSO and diluted 3 times to 20000.00 nM, 6666.67 nM, 2222.22 nM, 740.74 nM, 246.91 nM, 27.43 nM, 9.14 nM, 3.05 nM successively.

The lymphoma cell lines SU-DHL-5 and SU-DHL-6 were purchased from the American Type Culture Collection (ATCC).

Reagents: PRMI-1640, purchased from Invitrogen (USA); FBS, purchased from Invitrogen (USA); EDTA, purchased from Sigma (USA); CellTiter-Glo® Luminescent Cell Viability Assay Kit, purchased from Progema (USA); Backseal membrane, purchased from Perkin Elmer (USA).

2. Methods

Cell Resuscitation:

The cells were thawed in a 37° C. water bath and then transferred to 15 ml preheated medium. The cells were centrifuged at 1000 rpm for 5 min and the medium was discarded. The cells were resuspended in 15 ml fresh medium and transferred to T75 culture flask and incubated in an incubator at 37° C. with 5% $CO_2$. The medium was replaced with fresh medium 24 h later.

Cell Passages:

The resuscitated cells above were transferred to a 50 ml sterile centrifuge tube and centrifuged at 1000 rpm for 5 min. The medium was discarded, and the cells were dispersed uniformly and counted. The appropriate cell concentration was adjusted in 15 ml fresh medium and added to T75 culture flask. The flask was incubated in an incubator at 37° C. with 5% $CO_2$.

When the cells in the T75 culture flask grew to $1\times10^5$~$1\times10^6$ cells/ml, the cells were resuspended with fresh medium (RPMI-1640+20% FBS) and counted. The resuspended cells were adjusted to the following eight concentrations: $1\times10^4$ cells/ml, $2\times10^4$ cells/ml, $3\times10^4$ cells/ml, $5\times10^4$ cells/ml, $8\times10^4$ cells/ml, $1\times10^5$ cells/ml, $1.5\times10^5$ cells/ml, and $2\times10^5$ cells/ml. The above cell suspensions were added to 96-well cell culture plate, 100 μl each well ($1\times10^3$ cells/ml, $2\times10^3$ cells/ml, $3\times10^3$ cells/ml, $5\times10^3$ cells/ml, $8\times10^3$ cells/ml, $1\times10^4$ cells/ml, $1.5\times10^4$ cells/ml, and $2\times10^4$ cells/ml, respectively). Each concentration was done double in three plates. 72 h later, 100 μl CellTiter-Glo® Luminescent Cell Viability Assay buffer was added to test wells and shaken gently. 10 min later, the Assay plate was attached at the bottom by Backseal membrane and placed on Envison to detect the fluorescence reading. Cell survive (%) was calculated according to the formula: cell survive (%)=(Com−Min)/(Max−Min), wherein Max was the reading of solvent control group, Min was the reading of control group without cells, and Com was the reading of compound treatment group. $IC_{50}$ was fitted by XLfit processing of the data and results were shown in Table 2.

TABLE 2

| Cell Test compound | $IC_{50}$ (μM) | |
| --- | --- | --- |
| | SU-DHL-5 | SU-DHL-6 |
| Example 3 | 0.86 | — |
| Example 4 | 1.41 | 0.014 |
| Example 5 | 0.61 | — |
| Example 6 | 1.23 | — |
| Example 7 | 1.43 | — |

TABLE 2-continued

| Cell | IC$_{50}$ (μM) | |
|---|---|---|
| Test compound | SU-DHL-5 | SU-DHL-6 |
| Example 8 | 1.02 | — |
| Example 9 | 0.58 | — |
| Example 10 | 0.81 | 0.04 |
| Example 13 | 1.11 | — |
| Example 14 | 4.63 | 0.160 |
| Example 15 | 4.94 | — |
| Example 18 | 3.4 | — |

"—" means no detection.

As can be seen from the above experiments, the compounds of the present invention showed a good inhibitory activity for SU-DHL-5 and SU-DHL-6 lymphoma cells. Thus, it is very promising that the compounds of the present invention become therapeutic agents for lymphoma.

The inventors found that the compounds of the present invention have a very high selectivity to the subtype of PI3K kinase. In addition, the compounds of the present invention have an excellent bioavailability, a long half-life and a good druggability.

While the invention has been described in detail above, it will be understood by those skilled in the art that various modifications and changes can be made in the present invention without departing from the spirit and scope of the invention. The scope of the present invention is not to be limited to the detailed description given above, but is intended to be included in the claims.

The invention claimed is:

1. A compound represented by formula I or an stereoisomer, pharmaceutically acceptable salt or solvate thereof,

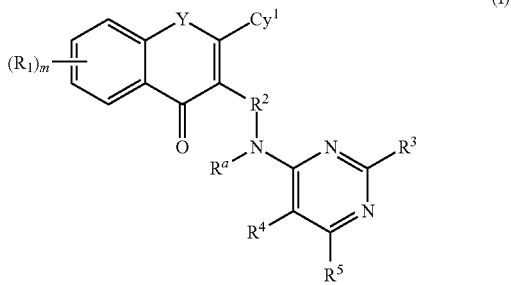

(I)

wherein,
- Y is selected from the group consisting of O and N($R^b$), wherein $R^b$ is selected from the group consisting of hydrogen, alkyl, haloalkyl and cycloalkyl;
- $R^1$ is selected from the group consisting of hydrogen, hydroxy, halogen, alkyl, haloalkyl, hydroxyalkyl, alkoxy, nitro, carboxyl, cyano, amino, monoalkylamino and dialkylamino; m is selected from the group consisting of 1, 2, 3 and 4;
- $R^2$ is selected from the group consisting of alkylene, alkenylene, alkynylene and cycloalkylene, which are optionally substituted with one or more selected from the group consisting of alkyl, haloalkyl, hydroxy, hydroxyalkyl, halogen, oxo, alkoxy, carboxyl, cyano, amino, monoalkylamino or dialkylamino;
- Cy$^1$ is selected from the group consisting of aryl and heteroaryl, which are optionally substituted with one or more selected from the group consisting of halogen, hydroxy, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino or alkylacylaminoalkyl;
- $R^a$ is selected from the group consisting of H and alkyl; and
- $R^3$, $R^4$ and $R^5$ are each independently selected from the group consisting of hydrogen, halogen, hydroxy, oxo, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino and alkylacylaminoalkyl.

2. The compound or the stereoisomer, pharmaceutically acceptable salt or solvate thereof according to claim 1, wherein
- Y is selected from the group consisting of O and N($R^b$), wherein $R^b$ is selected from the group consisting of hydrogen, methyl, ethyl, propyl, isopropyl, cyclopropyl, cyclobutyl, cyclopentyl and cyclohexyl;
- $R^1$ is selected from the group consisting of hydrogen, hydroxy, halogen, ($C_{1-3}$)alkyl, halo($C_{1-3}$)alkyl, hydroxy($C_{1-3}$)alkyl, ($C_{1-3}$)alkoxy, nitro, carboxyl, cyano, amino, mono-($C_{1-3}$)alkylamino and di-($C_{1-3}$)alkylamino, m is selected from the group consisting of 1, 2, 3 and 4;
- $R^2$ is selected from the group consisting of methylene, ethylene, propylene, cyclopropylene, cyclobutylene, cyclopentylene, cyclohexylene, vinylene, propenylene, butenylene, pentenylene, hexenylene, ethynylene, propynylene, butynylene, pentynylene and hexynylene, which are optionally substituted with one or more selected from the group consisting of methyl, ethyl, propyl, isopropyl and oxo;
- Cy$^1$ is selected from the group consisting of phenyl, pyridyl and pyrimidinyl, which are optionally substituted with one or more selected from the group consisting of halogen, hydroxy, amino, carboxyl, cyano, nitro, ($C_{1-3}$)alkyl, ($C_{3-6}$)cycloalkyl, ($C_{3-6}$)heterocycloalkyl, ($C_{1-3}$)alkoxy, halo($C_{1-3}$)alkyl, hydroxy($C_{1-3}$)alkyl, amino($C_{1-3}$)alkyl, carboxy($C_{1-3}$)alkyl, cyano($C_{1-3}$)alkyl, nitro($C_{1-3}$)alkyl, ($C_{3-6}$)cycloalkyl($C_{1-3}$)alkyl, ($C_{3-6}$)heterocycloalkyl($C_{1-3}$)alkyl, ($C_{1-3}$)alkoxy($C_{1-3}$)alkyl, mono-($C_{1-3}$)alkylamino, mono-($C_{1-3}$)alkylamino($C_{1-3}$)alkyl, di-($C_{1-3}$)alkylamino, di-($C_{1-3}$)alkylamino($C_{1-3}$)alkyl, ($C_{1-3}$)alkylacyl, ($C_{1-3}$)alkylacyl($C_{1-3}$)alkyl, ($C_{1-3}$)alkoxyacyl, ($C_{1-3}$)alkoxyacyl($C_{1-3}$)alkyl, ($C_{1-3}$)alkylacyloxy, ($C_{1-3}$)alkylacyloxy($C_{1-3}$)alkyl, aminoacyl, aminoacyl($C_{1-3}$)alkyl, mono-($C_{1-3}$)alkylaminoacyl, mono-($C_{1-3}$)alkylaminoacyl($C_{1-3}$)alkyl, di-($C_{1-3}$)alkylaminoacyl, di-($C_{1-3}$)alkylaminoacyl($C_{1-3}$)alkyl, ($C_{1-3}$)alkylacylamino or ($C_{1-3}$)alkyl acylamino($C_{1-3}$)alkyl;
- $R^a$ is selected from the group consisting of H, methyl, ethyl and propyl; and R³, R⁴ and R⁵ are each independently selected from the group consisting of hydrogen, halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino and $(C_{1-3})$alkylacylamino$(C_{1-3})$alkyl.

3. The compound or the stereoisomer, pharmaceutically acceptable salt or solvate thereof according to claim 1, wherein Y is selected from the group consisting of O and N(R$^b$), wherein R$^b$ is selected from the group consisting of hydrogen, methyl, ethyl, propyl, isopropyl and cyclopropyl.

4. The compound or the stereoisomer, pharmaceutically acceptable salt or solvate thereof according to claim 1, wherein R¹ is selected from the group consisting of hydrogen, hydroxyl, fluoro, chloro, methyl, ethyl, propyl, isopropyl, trifluoromethyl, hydroxymethyl, methoxy, ethoxy, nitro, carboxyl, cyano, amino, methylamino and dimethylamino; m is selected from the group consisting of 1, 2, 3 and 4.

5. The compound or the stereoisomer, pharmaceutically acceptable salt or solvate thereof according to claim 1, wherein R² is selected from the group consisting of methylene and ethylene, which are optionally substituted with one or more selected from the group consisting of methyl, ethyl, propyl, isopropyl and oxo group.

6. The compound or the stereoisomer, pharmaceutically acceptable salt or solvate thereof according to claim 1, wherein Cy¹ is phenyl, which is optionally substituted with one or more selected from the group consisting of halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino or $(C_{1-3})$alkylacylamino$(C_{1-3})$alkyl.

7. The compound or the stereoisomer, pharmaceutically acceptable salt or solvate thereof according to claim 1, wherein R³, R⁴ and R⁵ are each independently selected from the group consisting of hydrogen, halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1}$-3)alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino and $(C_{1-3})$alkylacylamino$(C_{1-3})$alkyl.

8. The compound or the stereoisomer, pharmaceutically acceptable salt or solvate thereof according to claim 1, wherein the compound is selected from the group consisting of:

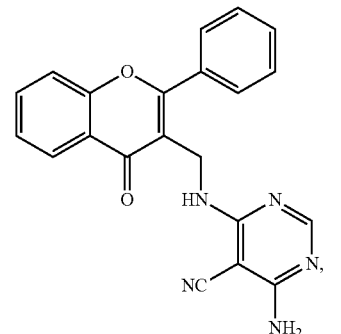

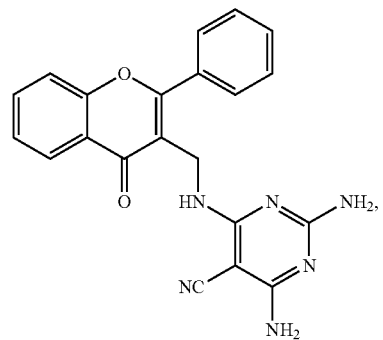

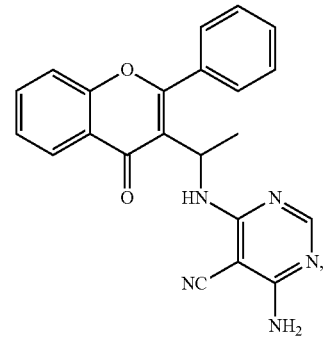

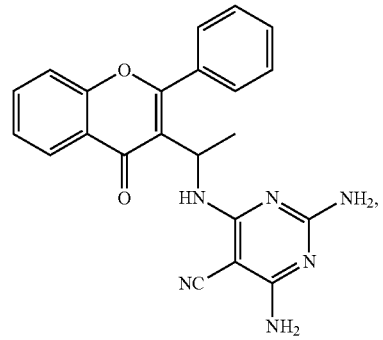

-continued
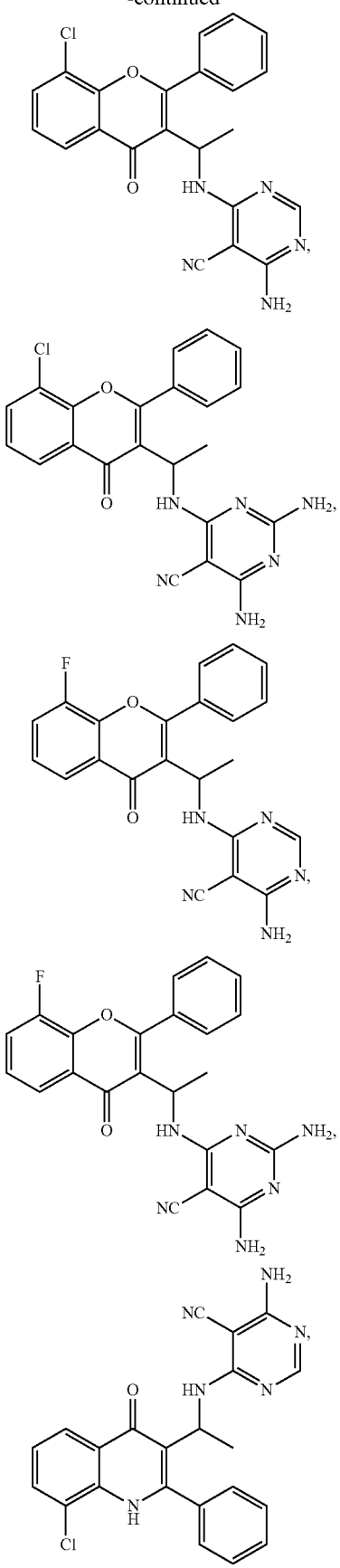
-continued
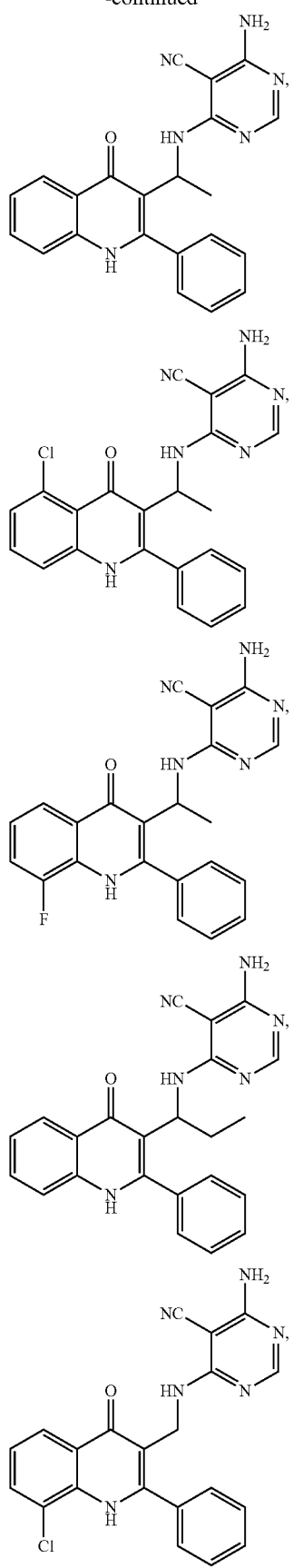

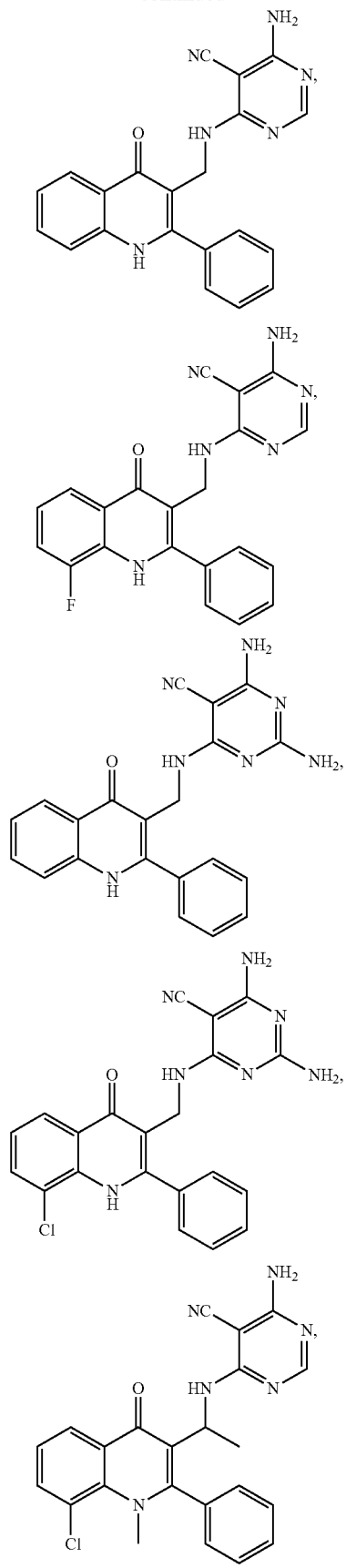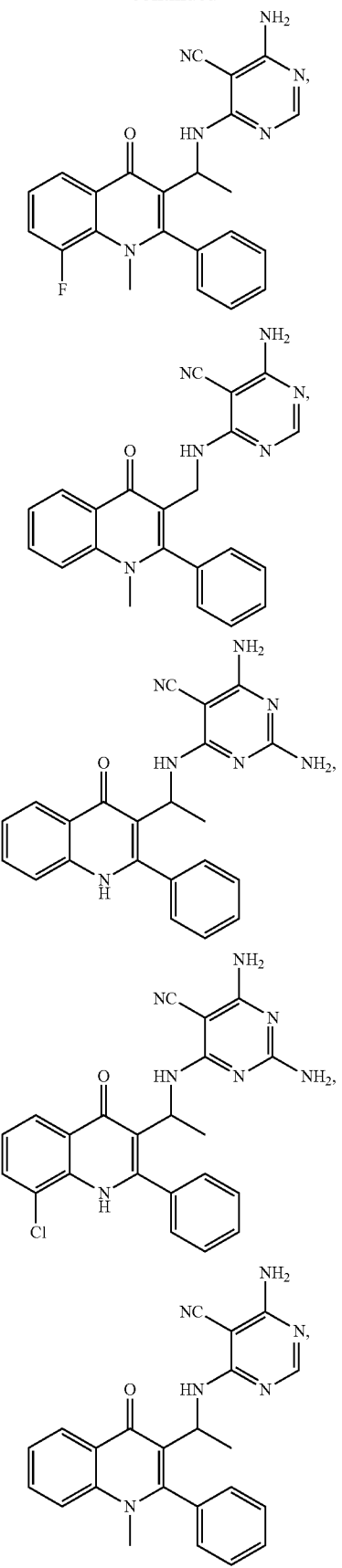

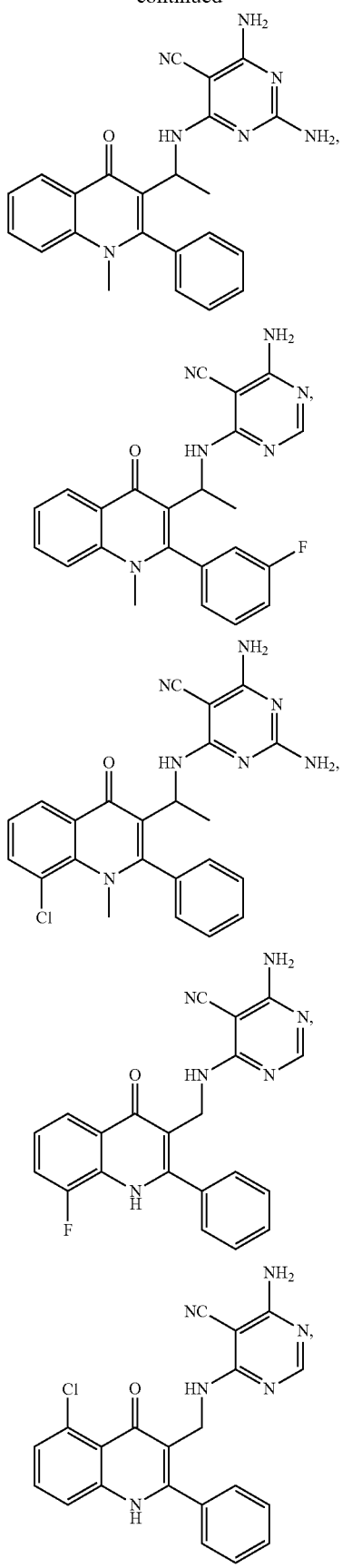

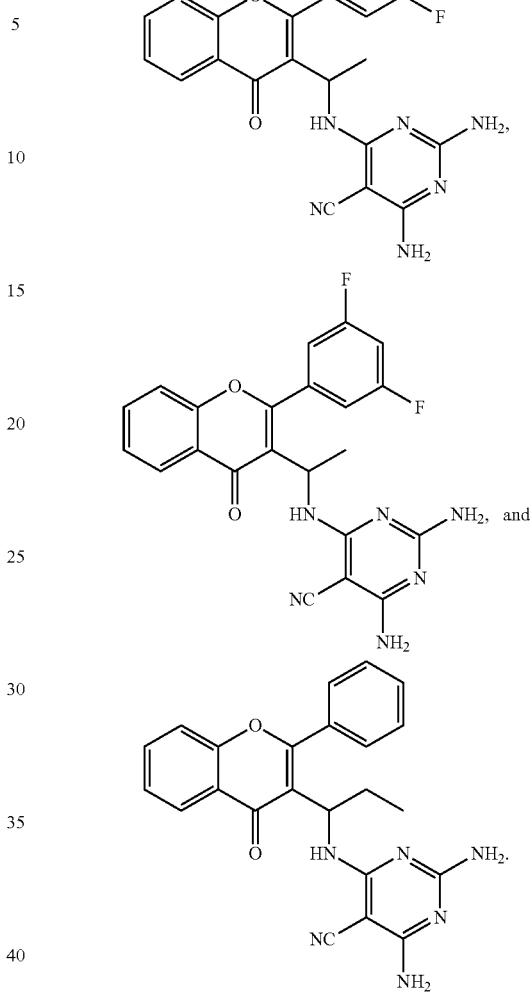

9. A pharmaceutical composition, comprising the compound or the stereoisomer, pharmaceutically acceptable salt or solvate thereof according to claim 1 and a pharmaceutically acceptable carrier, diluent or excipient.

10. The compound or the isomer, pharmaceutically acceptable salt, solvate or prodrug thereof according to claim 2, wherein $R^1$ is selected from the group consisting of hydrogen, hydroxyl, fluoro, chloro, methyl, ethyl, propyl, isopropyl, trifluoromethyl, hydroxymethyl, methoxy, ethoxy, nitro, carboxyl, cyano, amino, methylamino and dimethylamino; m is selected from the group consisting of 1, 2, 3 and 4.

11. The compound or the isomer, pharmaceutically acceptable salt, solvate or prodrug thereof according to claim 3, wherein $R^1$ is selected from the group consisting of hydrogen, hydroxyl, fluoro, chloro, methyl, ethyl, propyl, isopropyl, trifluoromethyl, hydroxymethyl, methoxy, ethoxy, nitro, carboxyl, cyano, amino, methylamino and dimethylamino; m is selected from the group consisting of 1, 2, 3 and 4.

12. The compound or the isomer, pharmaceutically acceptable salt, solvate or prodrug thereof according to claim 2, wherein $R^2$ is selected from the group consisting of methylene and ethylene, which are optionally substituted with one or more selected from the group consisting of methyl, ethyl, propyl, isopropyl and oxo group.

13. The compound or the isomer, pharmaceutically acceptable salt, solvate or prodrug thereof according to claim 3, wherein $R^2$ is selected from the group consisting of methylene and ethylene, which are optionally substituted with one or more selected from the group consisting of methyl, ethyl, propyl, isopropyl and oxo group.

14. The compound or the isomer, pharmaceutically acceptable salt, solvate or prodrug thereof according to claim 2, wherein $Cy^1$ is phenyl, which is optionally substituted with one or more selected from the group consisting of halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino or $(C_{1-3})$alkylacylamino$(C_{1-3})$alkyl.

15. The compound or the isomer, pharmaceutically acceptable salt, solvate or prodrug thereof according to claim 3, wherein $Cy^1$ is phenyl, which is optionally substituted with one or more selected from the group consisting of halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino or $(C_{1-3})$alkylacylamino$(C_{1-3})$alkyl.

16. The compound or the isomer, pharmaceutically acceptable salt, solvate or prodrug thereof according to claim 2, wherein Y is selected from the group consisting of O and $N(R^b)$, wherein $R^b$ is selected from the group consisting of hydrogen, methyl, ethyl, propyl, isopropyl and cyclopropyl;

$R^1$ is selected from the group consisting of hydrogen, hydroxyl, fluoro, chloro, methyl, ethyl, propyl, isopropyl, trifluoromethyl, hydroxymethyl, methoxy, ethoxy, nitro, carboxyl, cyano, amino, methylamino and dimethylamino; m is selected from the group consisting of 1, 2, 3 and 4;

$R^2$ is selected from the group consisting of methylene and ethylene, which are optionally substituted with one or more selected from the group consisting of methyl, ethyl, propyl, isopropyl and oxo group; and $Cy^1$ is phenyl, which is optionally substituted with one or more selected from the group consisting of halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkyl acyl oxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino or $(C_{1-3})$alkylacylamino$(C_{1-3})$alkyl.

17. The compound or the isomer, pharmaceutically acceptable salt, solvate or prodrug thereof according to claim 3, wherein $R^3$, $R^4$ and $R^5$ are each independently selected from the group consisting of hydrogen, halogen, hydroxy, amino, carboxyl, cyano, nitro, $(C_{1-3})$alkyl, $(C_{3-6})$cycloalkyl, $(C_{3-6})$heterocycloalkyl, $(C_{1-3})$alkoxy, halo$(C_{1-3})$alkyl, hydroxy$(C_{1-3})$alkyl, amino$(C_{1-3})$alkyl, carboxy$(C_{1-3})$alkyl, cyano$(C_{1-3})$alkyl, nitro$(C_{1-3})$alkyl, $(C_{3-6})$cycloalkyl$(C_{1-3})$alkyl, $(C_{3-6})$heterocycloalkyl$(C_{1-3})$alkyl, $(C_{1-3})$alkoxy$(C_{1-3})$alkyl, mono-$(C_{1-3})$alkylamino, mono-$(C_{1-3})$alkylamino$(C_{1-3})$alkyl, di-$(C_{1-3})$alkylamino, di-$(C_{1-3})$alkylamino$(C_{1-3})$alkyl, $(C_{1-3})$alkylacyl, $(C_{1-3})$alkylacyl$(C_{1-3})$alkyl, $(C_{1-3})$alkoxyacyl, $(C_{1-3})$alkoxyacyl$(C_{1-3})$alkyl, $(C_{1-3})$alkylacyloxy, $(C_{1-3})$alkylacyloxy$(C_{1-3})$alkyl, aminoacyl, aminoacyl$(C_{1-3})$alkyl, mono-$(C_{1-3})$alkylaminoacyl, mono-$(C_{1-3})$alkylaminoacyl$(C_{1-3})$alkyl, di-$(C_{1-3})$alkylaminoacyl, di-$(C_{1-3})$alkylaminoacyl$(C_{1-3})$alkyl, $(C_{1-3})$alkylacylamino and $(C_{1-3})$alkylacylamino$(C_{1-3})$alkyl.

\* \* \* \* \*

UNITED STATES PATENT AND TRADEMARK OFFICE
CERTIFICATE OF CORRECTION

PATENT NO.        : 10,077,258 B2
APPLICATION NO.   : 15/551679
DATED             : September 18, 2018
INVENTOR(S)       : Yong Wang et al.

Page 1 of 2

It is certified that error appears in the above-identified patent and that said Letters Patent is hereby corrected as shown below:

In the Claims

In Claim 7, Column 61, Line 67, delete "$(C_{1-3})$alkoxyacyl$(C_{1-3})$alkyl" and insert --$(C_{1-3})$alkoxyacyl$(C_{1-3})$alkyl-- therefor.

In Claim 10, Column 68, Lines 48-49, delete "The compound or the isomer, pharmaceutically acceptable salt, solvate or prodrug thereof" and insert --The compound or the stereoisomer, pharmaceutically acceptable salt or solvate thereof-- therefor.

In Claim 11, Column 68, Lines 56-57, delete "The compound or the isomer, pharmaceutically acceptable salt, solvate or prodrug thereof" and insert --The compound or the stereoisomer, pharmaceutically acceptable salt or solvate thereof-- therefor.

In Claim 12, Column 68, Lines 64-65, delete "The compound or the isomer, pharmaceutically acceptable salt, solvate or prodrug thereof" and insert --The compound or the stereoisomer, pharmaceutically acceptable salt or solvate thereof-- therefor.

In Claim 13, Column 69, Lines 3-4, delete "The compound or the isomer, pharmaceutically acceptable salt, solvate or prodrug thereof" and insert --The compound or the stereoisomer, pharmaceutically acceptable salt or solvate thereof-- therefor.

In Claim 14, Column 69, Lines 9-10, delete "The compound or the isomer, pharmaceutically acceptable salt, solvate or prodrug thereof" and insert --The compound or the stereoisomer, pharmaceutically acceptable salt or solvate thereof-- therefor.

In Claim 14, Column 69, Line 17, delete "$(C_{3-6})$cycloalkyl$(C_{1-3})$alkyl" and insert --$(C_{3-6})$cycloalkyl$(C_{1-3})$alkyl-- therefor.

Signed and Sealed this
Sixth Day of November, 2018

Andrei Iancu
*Director of the United States Patent and Trademark Office*

CERTIFICATE OF CORRECTION (continued)
U.S. Pat. No. 10,077,258 B2

In Claim 15, Column 69, Lines 28-29, delete "The compound or the isomer, pharmaceutically acceptable salt, solvate or prodrug thereof" and insert --The compound or the stereoisomer, pharmaceutically acceptable salt or solvate thereof-- therefor.

In Claim 15, Column 69, Line 36, delete "$(C_3\text{-}6)$cycloalkyl$(C_{1\text{-}3})$alkyl" and insert --$(C_{3\text{-}6})$cycloalkyl$(C_{1\text{-}3})$alkyl-- therefor.

In Claim 16, Column 69, Lines 47-48, delete "The compound or the isomer, pharmaceutically acceptable salt, solvate or prodrug thereof" and insert --The compound or the stereoisomer, pharmaceutically acceptable salt or solvate thereof-- therefor.

In Claim 17, Column 70, Lines 32-33, delete "The compound or the isomer, pharmaceutically acceptable salt, solvate or prodrug thereof" and insert --The compound or the stereoisomer, pharmaceutically acceptable salt or solvate thereof-- therefor.